(12) United States Patent
Bremer et al.

(10) Patent No.: US 6,171,664 B1
(45) Date of Patent: Jan. 9, 2001

(54) TOLAN DERIVATIVES, AND LIQUID-CRYSTALLINE MEDIUM

(75) Inventors: Matthias Bremer, Darmstadt; Detlef Pauluth, Ober-Ramstadt; Harald Hirschmann, Darmstadt, all of (DE)

(73) Assignee: Merck Patent Gesellschaft mit beschrankter Haftung (DE)

( * ) Notice: Under 35 U.S.C. 154(b), the term of this patent shall be extended for 0 days.

(21) Appl. No.: 09/334,600

(22) Filed: Jun. 17, 1999

(30) Foreign Application Priority Data

Jun. 18, 1998 (DE) .............................................. 198 27 129

(51) Int. Cl.[7] ...................... C07C 43/176; C07C 43/192; C07C 25/24; C09K 19/34; C09K 19/30; C07D 319/06

(52) U.S. Cl. ................ 428/1.1; 252/299.61; 252/299.63; 549/369; 568/610; 568/647; 570/127; 570/129; 570/131

(58) Field of Search ........................ 252/299.61, 299.66, 252/299.63; 570/127, 129, 131; 568/647, 610; 549/369; 428/1.1

(56) References Cited

FOREIGN PATENT DOCUMENTS

98/07672 * 2/1998 (WO) .

* cited by examiner

*Primary Examiner*—Shean C. Wu
(74) *Attorney, Agent, or Firm*—Millen, White, Zelano, & Branigan, P.C.

(57) ABSTRACT

The invention relates to tolan derivatives of the formula I

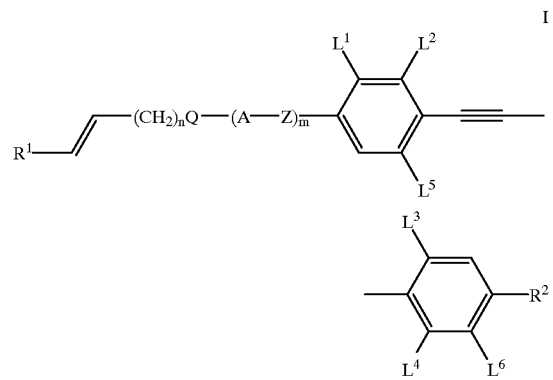

in which $R^1$, $R^2$, A, Z, $L^1$, $L^2$, $L^3$, $L^4$, $L^5$, $L^6$, Q, m and n are as defined herein.

30 Claims, No Drawings

TOLAN DERIVATIVES, AND LIQUID-CRYSTALLINE MEDIUM

The invention relates to novel tolan derivatives of the formula I

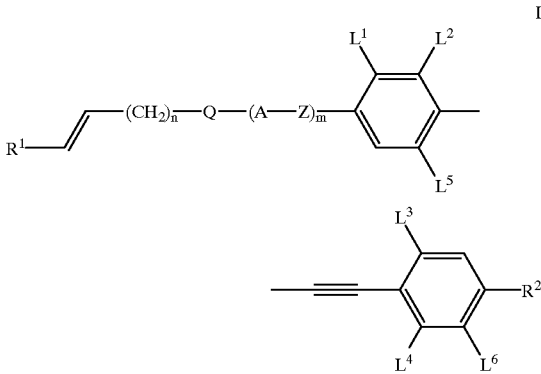

in which
$R^1$ is H or an alkyl radical having 1–12 carbon atoms which is unsubstituted, monosubstituted by CN or $CF_3$ or monosubstituted to perhalosubstituted by halogen, where one or more non-adjacent $CH_2$ groups in these radicals may also, independently of one another, each be replaced by —CH=CH—, —O—, —S—, —CO—,

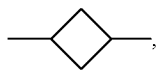

—CO—O—, —O—CO— or —O—CO—O—,
$R^2$ is alkyl or alkoxy having 1 to 10 carbon atoms which is unsubstituted or monosubstituted to perhalosubstituted by halogen; alkenyl or alkenyloxy having 2 to 10 carbon atoms which is unsubstituted or at least monosubstituted by —CN, —$CF_3$ or —F; or —F, —Cl, —$CF_3$, —$OCHF_2$, —$OCF_3$, —$OCHFCF_3$ or —$OCF_2CF_3$,
$L^1, L^2, L^3, L^4, L^5, L^6$ are each, independently of one another, H or F,
Q is —O— or a single bond
A is a trans-1,4-cyclohexylene radical, in which, in addition, one or more non-adjacent $CH_2$ groups may be replaced by —O— and/or —S—, or 1,4-cyclohexenylene, where the rings may be substituted by CN, Cl or F,
Z is —CO—O—, —O—CO—, —$CH_2$O—, —O—, —O—$CH_2$—, —$CH_2CH_2$—, —CH=CH—, —C≡C— or a single bond,
when there are more than one A or Z groups, they may have the above meanings independently from one another,
n is 0, 1, 2, 3 or 4 and
m is 0, 1 or 2,
with the provisos that compounds of the formula I in which either
a) m is 0 and simultaneously $R^2$ is alkyl or alkoxy, or
b) m is 0 and simultaneously $L^1, L^2, L^3, L^4, L^5$ and $L^6$ are H, or
c) $L^6$ is F and simultaneously $L^3$ is H, or
d) $L^2$ and $L^5$ are F and simultaneously $L^3$ and $L^4$ are H
are excluded.

The invention also relates to the use of the compounds of the formula I as components of liquid-crystalline media, and to liquid-crystal and electro-optical display elements which contain the liquid-crystalline media according to the invention.

The compounds of the formula I can be used as components of liquid-crystalline media, in particular for displays based on the principle of the twisted cell, the guest-host effect, the effect of deformation of aligned phases (DAP) or electrically controlled birefringence (ECB) or the effect of dynamic scattering.

BACKGROUND OF THE INVENTION

The substances employed hitherto for this purpose all have certain disadvantages, for example inadequate stability to the action of heat, light or electric fields, or unfavorable elastic and/or dielectric properties.

The compounds excepted by the proviso are compounds of the formula I without lateral fluorination in which m is 0. These bicyclic tolans which are disclosed, for example, in JP 040 216 40, have relatively low solubility and are therefore less suitable for practical applications.

Compounds of the formula I in which m is 0 are disclosed, for example, in JP 063 296 31, but this specification only mentions tolans which have alkyl or alkoxy terminal groups. Compounds of this type exhibit a relatively low optical anisotropy value and a relatively low clearing point and are likewise excepted by the proviso.

Although fluorinated compounds of the formula I containing terminal alkenyl radicals or polar radicals in which m is 0 are amongst the compounds covered by the very broad generic claims in EP 0 648 723 and JP 093 019 01, these documents make absolutely no mention of the advantageous specific lateral fluorination of the compounds of the formula I. EP 543 244, JP 080 601 58, JP 072 343 9 and JP 080 536 74 describe tricyclic fluorinated tolan derivatives, but these likewise differ from the compounds of the formula I according to the invention through the position of the lateral fluorination.

SUMMARY OF THE INVENTION

The invention had an object of finding novel, stable, liquid-crystalline or mesogenic compounds of high optical anisotropy at the same time as low negative to highly positive dielectric anisotropy which are suitable as components of liquid-crystalline media, in particular for TFT and STN displays.

Upon further study of the specification and appended claims, further objects and advantages of this invention will become apparent to those skilled in the art.

It has now been found that the compounds of the formula I are eminently suitable as components of liquid-crystalline media. They can be used to obtain stable liquid-crystalline media, in particular suitable for TFT or STN displays. The novel compounds are distinguished in particular by high thermal stability, which is advantageous for a high holding ratio, and exhibit favorable clearing point values. Preferred compounds of the formula I have a broad nematic phase and a dielectric anisotropy of between −3 and +3.

The provision of compounds of the formula I very generally considerably broadens the range of liquid-crystalline substances which are suitable, from various applicational points of view, for the preparation of liquid-crystalline mixtures.

The compounds of the formula I have a broad range of applications. Depending on the choice of substituents, these compounds can serve as base materials of which liquid-crystalline media are predominantly composed; however, it is also possible to add liquid-crystalline base materials from other classes of compounds to compounds of the formula I in order, for example, to modify the dielectric and/or optical anisotropy of a dielectric of this type and/or to optimize its threshold voltage and/or its viscosity. The meaning of the formula I covers all isotopes of the chemical elements bound in the compounds of the formula I. In enantiomerically pure or enriched forms, the compounds of the formula I are also suitable as chiral dopants and in general for producing chiral mesophases.

In particular, the compounds according to the invention are distinguished by very high optical anisotropy in combination with high clearing point values and excellent solubility in a wide variety of host mixtures.

In the pure state, the compounds of the formula I are colorless and form liquid-crystalline mesophases in a temperature range which is favorably located for electro-optical use. They are stable chemically, thermally and to light.

Aspects of the invention thus include the compounds of the formula I and the use of these compounds as components of liquid-crystalline media. The invention furthermore relates to liquid-crystalline media containing at least one compound of the formula I, and to liquid-crystal display elements, in particular electro-optical display elements, which contain media of this type.

Above and below, $R^1$, $R^2$, A, Z, $L^1$, $L^2$, $L^3$, $L^4$, $L^5$, $L^6$, Q, m and n are as defined above, unless expressly stated otherwise.

If the radical A occurs more than once, it can have the same or different meanings. The same applies to the group Z.

The following group of compounds of the formulae IA to IL are preferred embodiments of the invention.

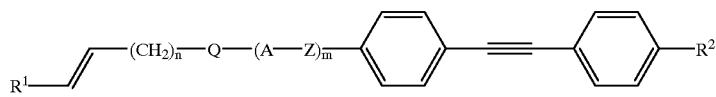

IA

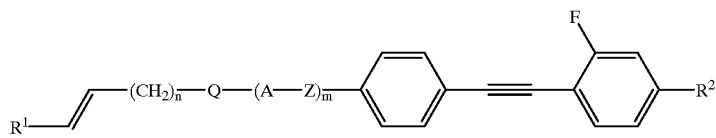

IB

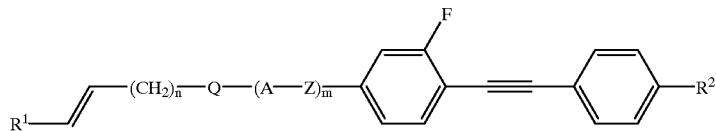

IC

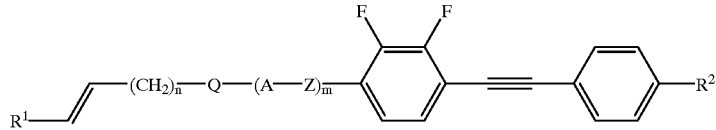

ID

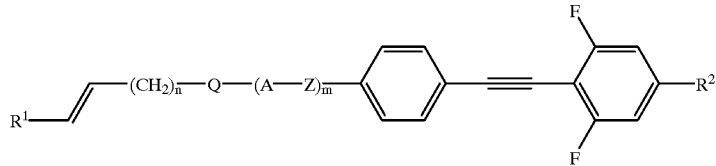

IE

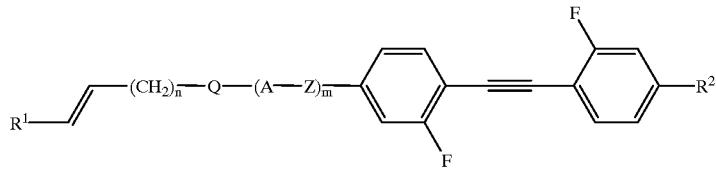

IF

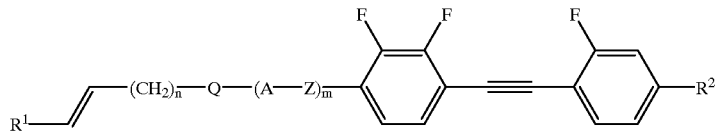

IG

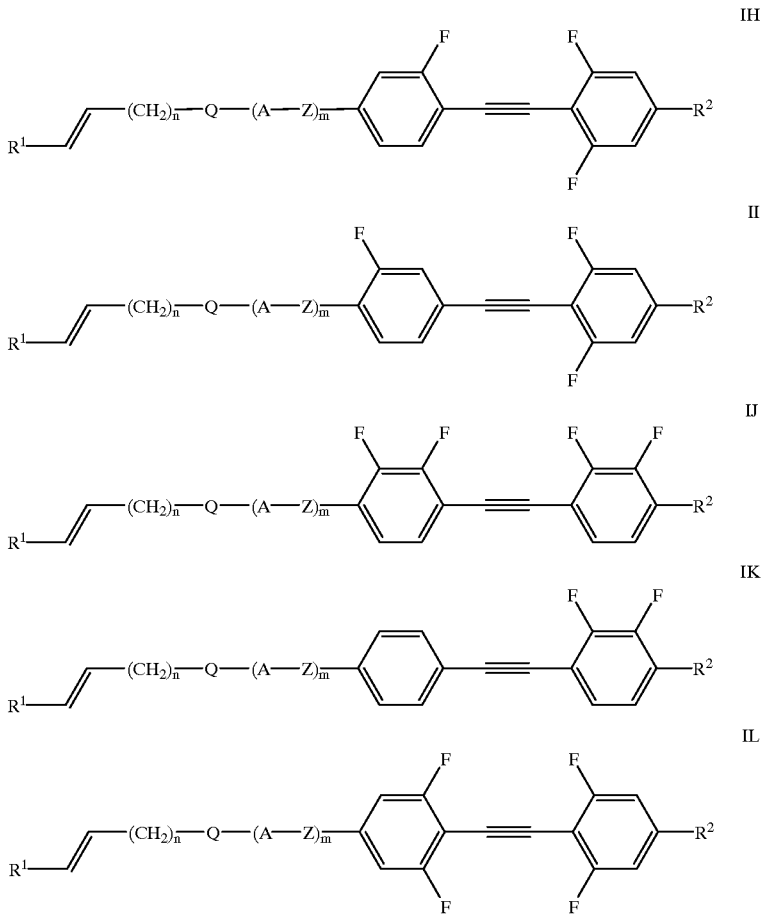

in which $R^1$, $R^2$, A, Z, Q, m and n are as defined above.

$R^2$ is preferably F, $OCF_3$, straight-chain alkyl or alkoxy having 1 to 10 carbon atoms, alkenyl or alkenyloxy having 2 to 10 carbon atoms, in particular, F, alkyl, alkoxy or alkenyl. Very particular preference is given to alkyl or alkoxy.

In the compounds of the formulae above and below, $R^1$ is preferably H, straight-chain alkyl having 1 to 10 carbon atoms or alkenyl having 2 to 10 carbon atoms, furthermore preferably alkoxy having 1 to 10 carbon atoms.

Q is preferably a single bond.

A is preferably

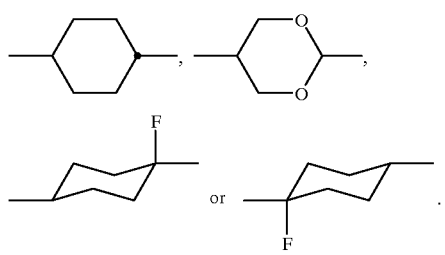

A is particularly preferably

n is preferably 0, 1 or 2, particularly preferably 0 or 2. m is 0 or 1, particularly preferably 1. Z is preferably —$CH_2CH_2$—, —CH=CH— or a single bond, particularly preferably a single bond, —$CH_2$—$CH_2$— or —COO—. Z is very particularly preferably a single bond or —COO—.

Particular preference is given to compounds of the formula I which are characterized in that $R^1$ is H, straight-chain alkyl or alkoxy having 1 to 7 carbon atoms or alkenyl having 2 to 7 carbon atoms and $R^2$ is alkyl or alkoxy having 1 to 7 carbon atoms, alkenyl or alkenyloxy having 2 to 10 carbon atoms, —F, —$OCHF_2$ or —$OCF_3$.

Preference is furthermore given to compounds of the formula I in which m is 1 and at least one of the radicals $L^1$, $L^2$, $L^3$ and $L^4$ is F.

Preference is furthermore given to compounds of the formula I in which $L^6$ and $L^5$ are H.

In the compounds of the formula I in which m is 1 and $L^3$ and/or $L^4$ are F, $R^2$ is preferably alkyl, alkoxy, alkenyl or alkenyloxy.

In the compounds of the formula I in which m is 0 and $L^3$ and/or $L^4$ are F, $R^2$ is preferably alkenyl or alkenyloxy.

The 1,4-cyclohexenylene group preferably has the following structures:

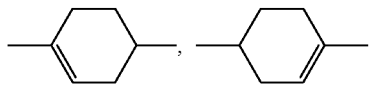
The following group of compounds of the subformulae I1 to I12 represents preferred embodiments of the invention:
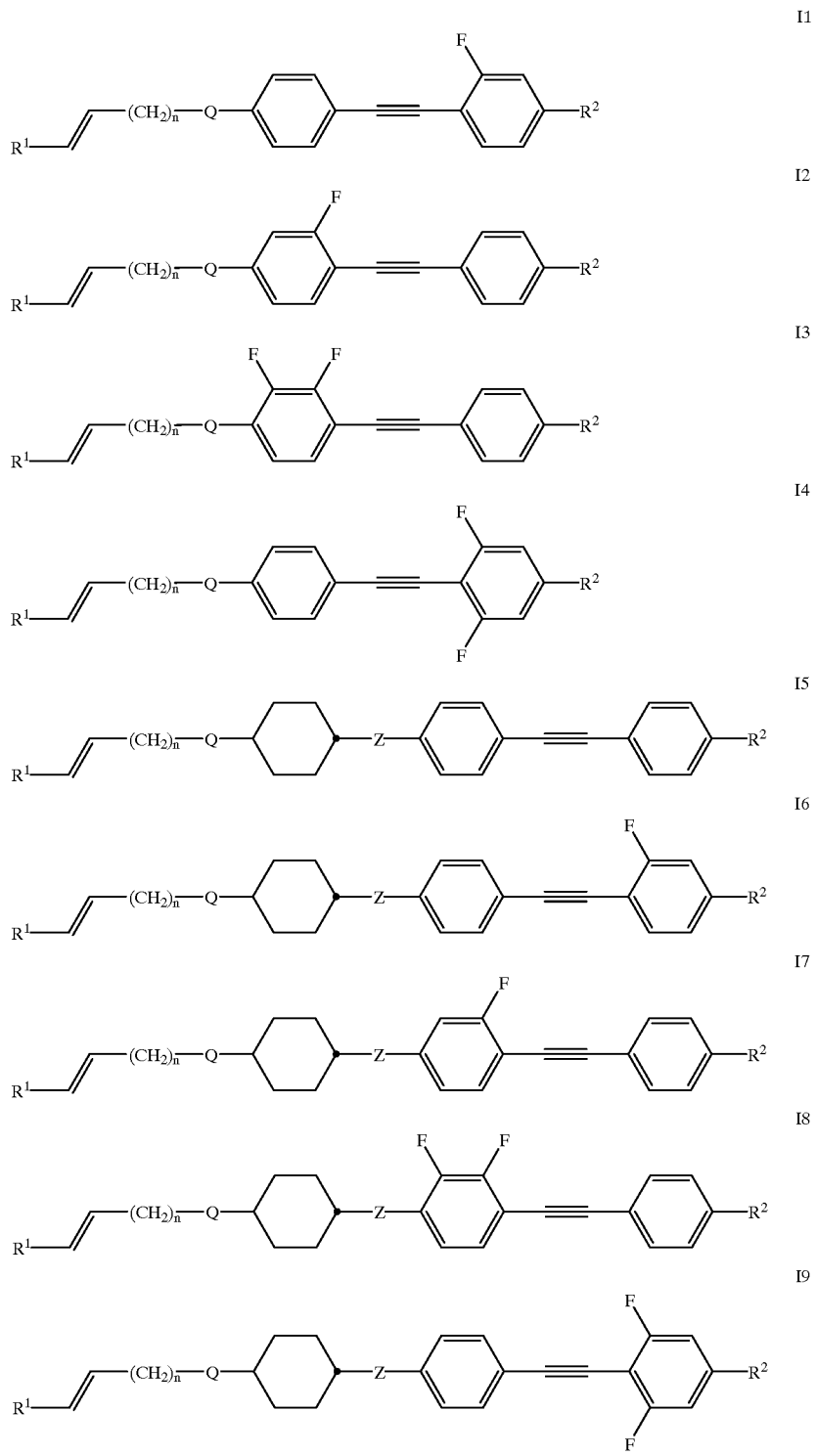

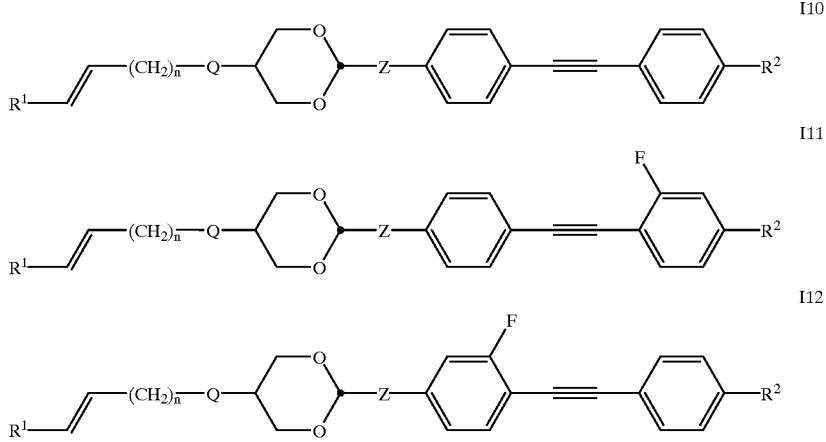

If R¹ and/or R² in the formulae above and below are an alkyl radical and/or an alkoxy radical, this can be straight-chain or branched. It is preferably straight-chain, has 2, 3, 4, 5, 6, or 7 carbon atoms and accordingly is preferably ethyl, propyl, butyl, pentyl, hexyl, heptyl, ethoxy, propoxy, butoxy, pentyloxy, hexyloxy or heptyloxy, furthermore methyl, octyl, nonyl, decyl, undecyl, dodecyl, tridecyl, tetradecyl, pentadecyl, methoxy, octyloxy, nonyloxy, decyloxy, undecyloxy, dodecyloxy, tridecyloxy or tetradecyloxy.

Oxaalkyl is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl.

If R¹ is an alkyl radical in which one $CH_2$ group has been replaced by —CH=CH— or R² is an alkenyl radical, these can be straight-chain or branched. They are preferably straight-chain and have 2 to 10 carbon atoms. Accordingly, they are in particular vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, dec-1-, -2-, -3-, -4-, -5-, -6-, -7-, -8- or -9-enyl. Preferably, the double bond in such compounds appears in a trans configuration; this is also preferred when Z contains a double bond.

If R¹ is an alkyl radical in which one $CH_2$ group has been replaced by —O— and another has been replaced by —CO—, these are preferably adjacent. These thus contain an acyloxy group —CO—O— or an oxycarbonyl group —O—CO—. These are preferably straight-chain and have 2 to 6 carbon atoms.

Accordingly, they are in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If R¹ is an alkyl radical in which one $CH_2$ group has been replaced by unsubstituted or substituted —CH=CH— and an adjacent $CH_2$ group has been replaced by CO or CO—O or O—CO—, this can be straight-chain or branched. It is preferably straight-chain and has 4 to 13 carbon atoms. Accordingly, it is in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

If R¹ is an alkyl or alkenyl radical which is monosubstituted by CN or $CF_3$, this radical is preferably straight-chain and the substitution by CN or $CF_3$ is in the ω-position.

If R¹ is an alkyl or alkenyl radical which is at least monosubstituted by halogen, this radical is preferably straight-chain and halogen is preferably F or Cl. In the case of multiple substitution, halogen is preferably F. The resultant radicals also include perfluorinated radicals. In the case of monosubstitution, the fluorine or chlorine substituent can be in any desired position, but is preferably in the ω-position.

Compounds of the formula I containing a branched wing group R¹ may occasionally be of importance owing to better solubility in the customary liquid-crystalline base materials, but in particular as chiral dopants if they are optically active. Smectic compounds of this type are suitable as components of ferroelectric materials.

Branched groups of this type generally contain not more than one chain branch. Preferred branched radicals R¹ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentyloxy, 3-methylpentyloxy, 2-ethylhexyloxy, 1-methylhexyloxy or 1-methylheptyloxy.

Formula I covers the racemates of these compounds and the optical antipodes, and mixtures thereof.

Of these compounds of the formula I and the subformulae, preference is given to those in which at least one of the radicals present therein has one of the preferred meanings indicated.

Some very particularly preferred smaller groups of compounds of the formula I are those of the subformulae I14 to I 80:

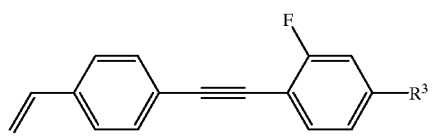
I14
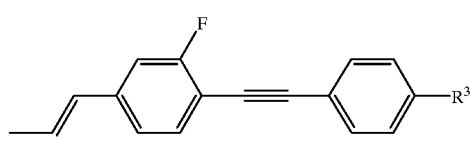
I15
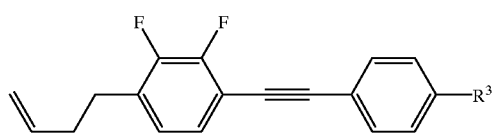
I16
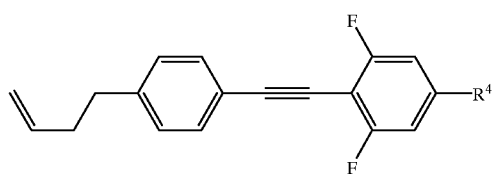
I17
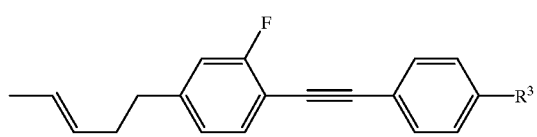
I18
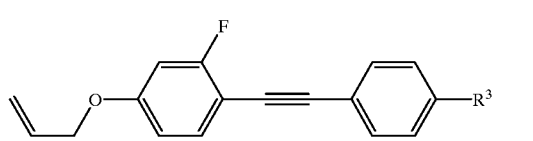
I19
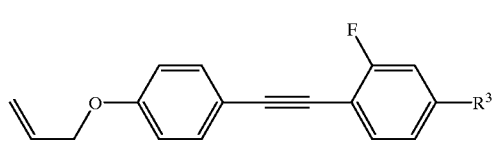
I20
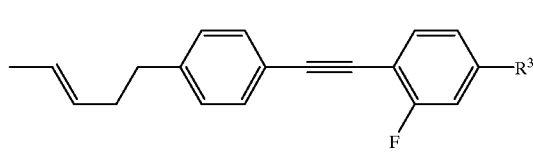
I21
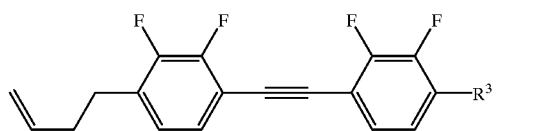
I22
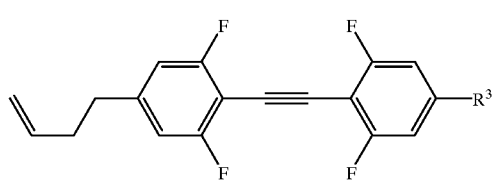
I23

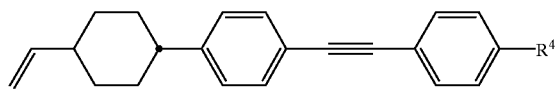
I24
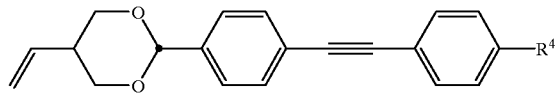
I25
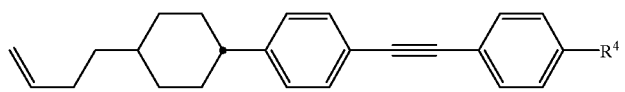
I26
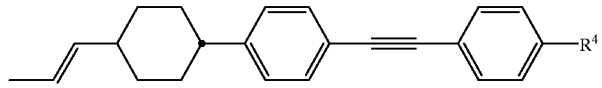
I27
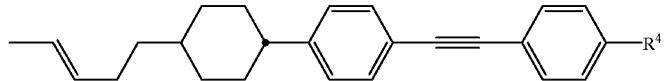
I28
I29
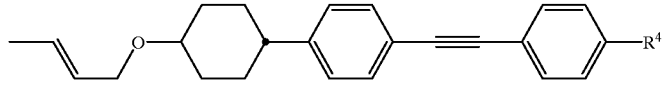
I30
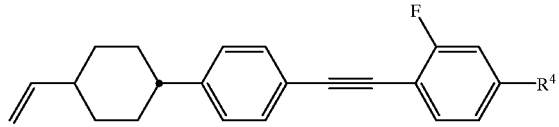
I31
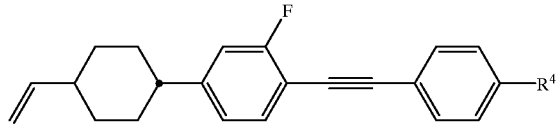
I32
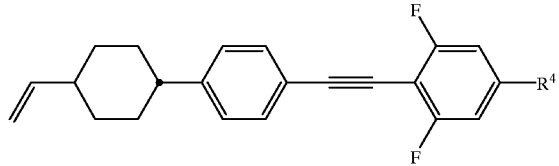
I33
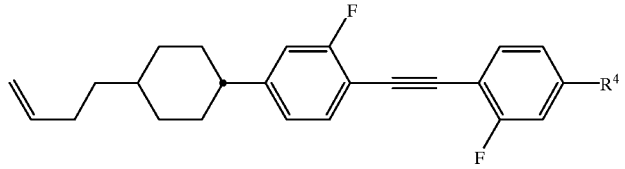
I34
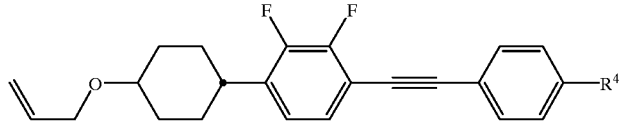
I35

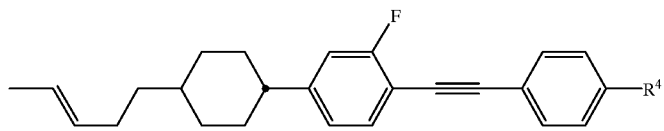
I36
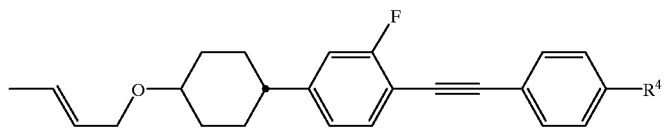
I37
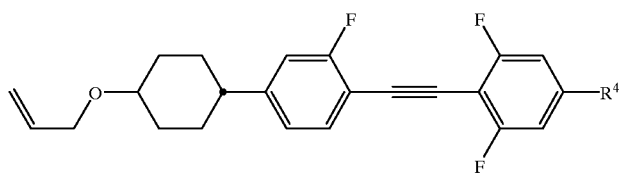
I38
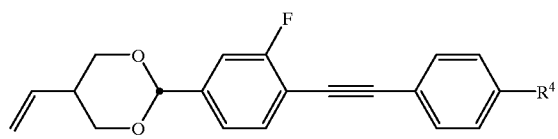
I39
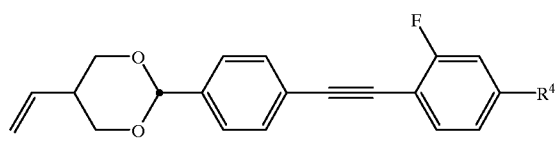
I40
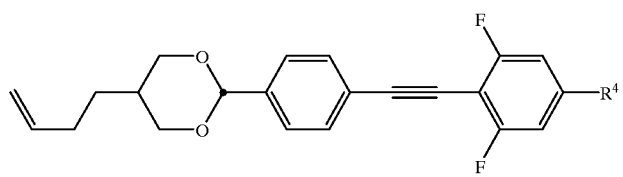
I41
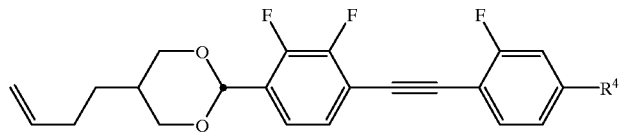
I42
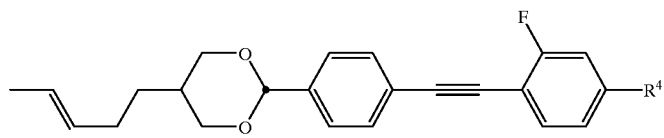
I43
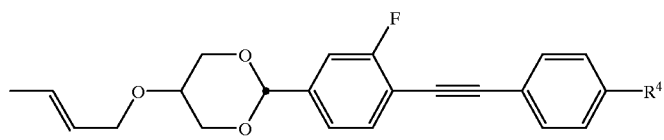
I44
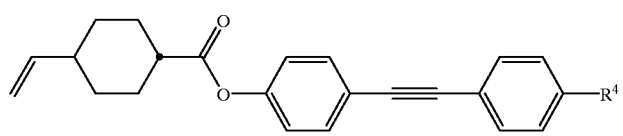
I45

I46
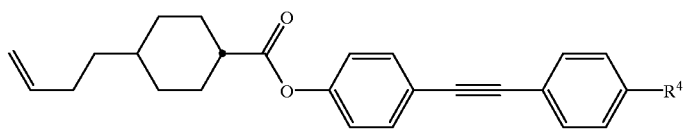
I47
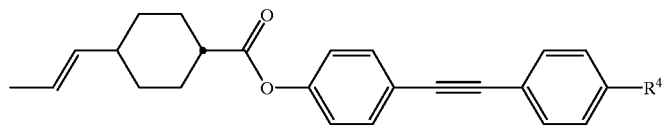
I48
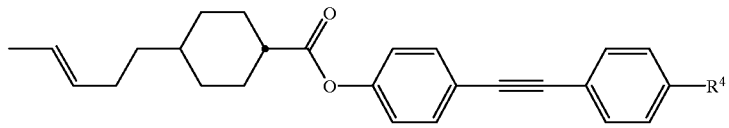
I49
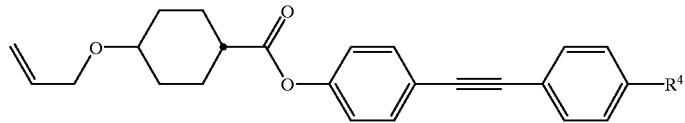
I50
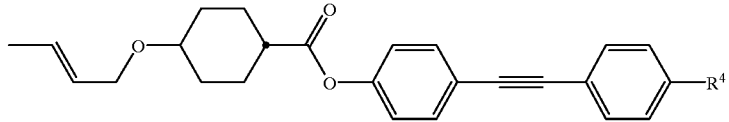
I51
I52
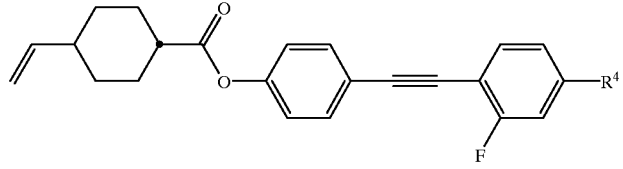
I53
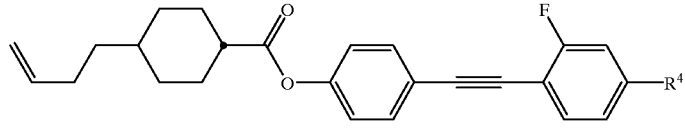
I54
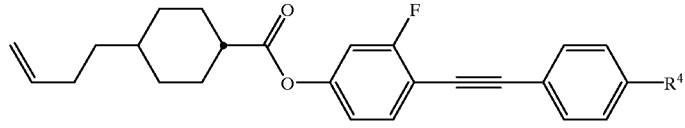
I55
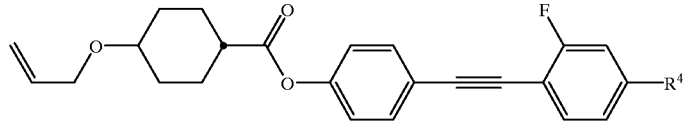

-continued
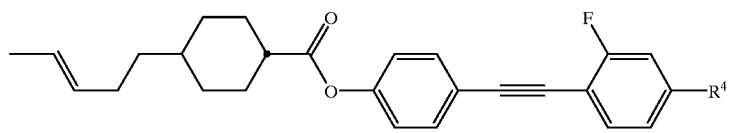
I56
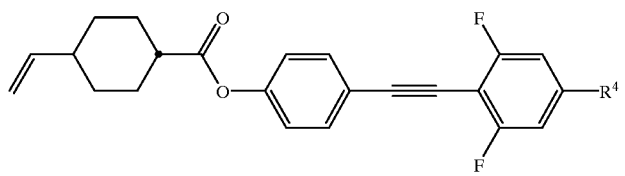
I57
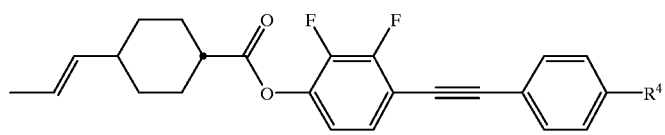
I58
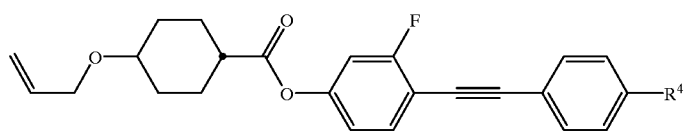
I59
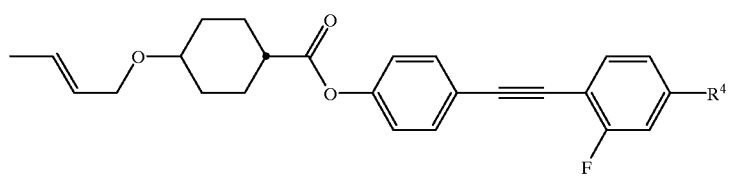
I60
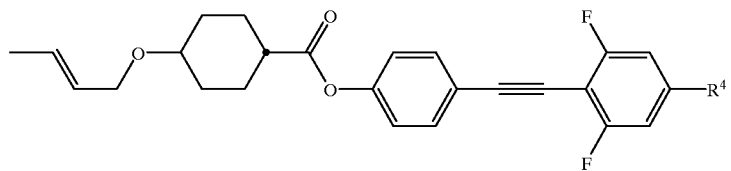
I61
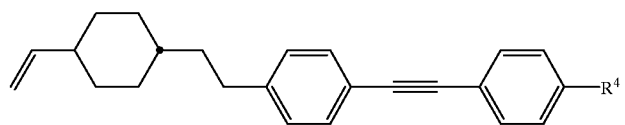
I62
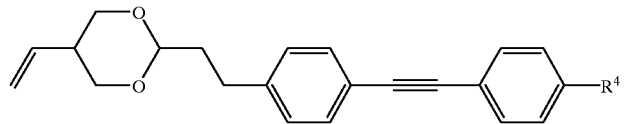
I63
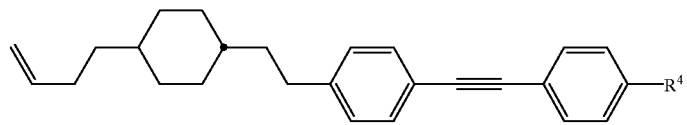
I64
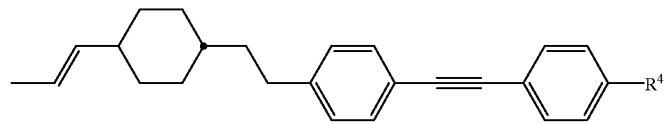
I65

-continued
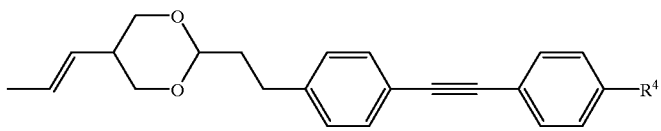
I66
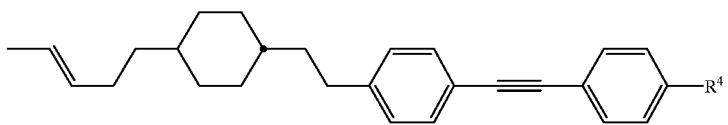
I67
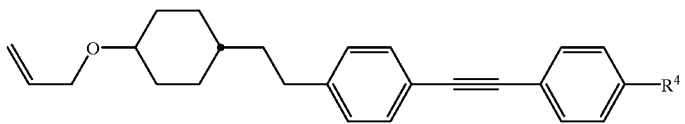
I68
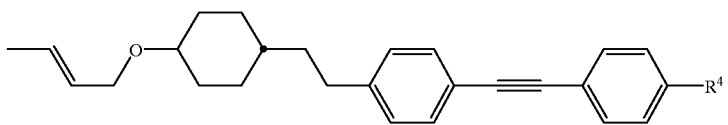
I69
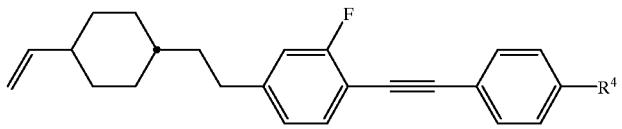
I70
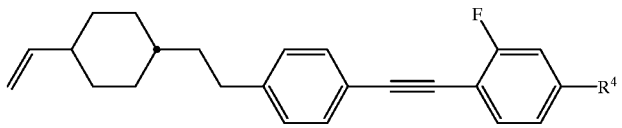
I71
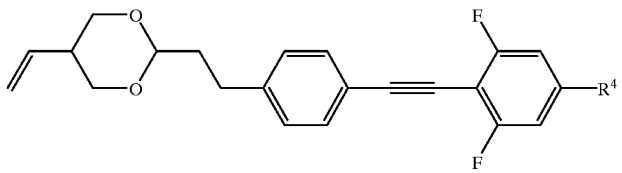
I72
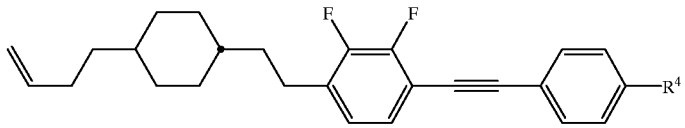
I73
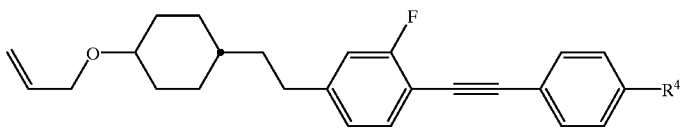
I74
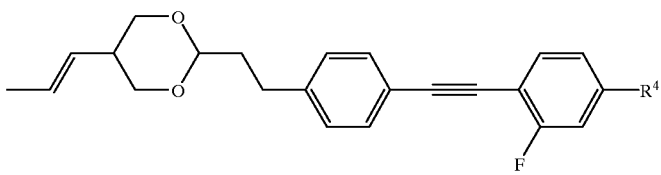
I75

-continued

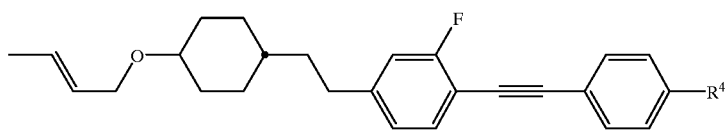

I76

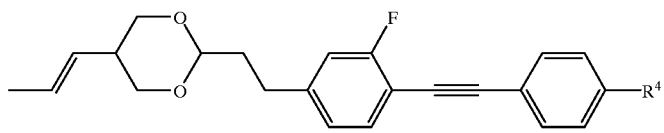

I77

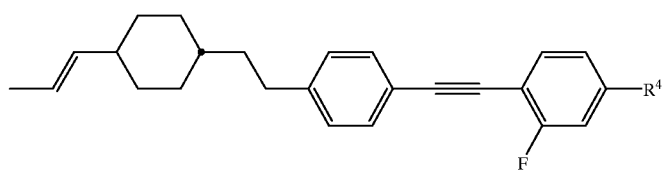

I78

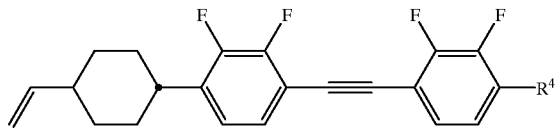

I79

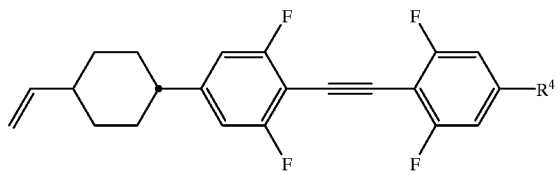

I80 in which
R³ is F, Cl, —CF₃, OCF₃, OCHF₂, OCF₂CF₃, OCHF₂CF₃, alkenyl or alkenyloxy and
R⁴ is alkyl, alkoxy, alkenyl, alkenyloxy, F, Cl, OCF₃, OCHF₂, OCF₂CF₃ or OCHF₂CF₃.

R³ in the compounds of the formulae I14–I23 is preferably F, OCF₃, alkenyl or alkenyloxy
R⁴ in the compounds of the formulae I24–I80 is preferably alkyl, alkoxy, alkenyl or alkenyloxy.
Very particularly preferred compounds from this group are those of the formulae I22, I26, I28, I29, I43, I46, I50 and I65.

The compounds of the formula I are prepared by methods known per se, as described in the literature (for example in the standard works, such as Houben-Weyl, Methoden der Organischen Chemie [Methods of Organic Chemistry], Georg-Thieme-Verlag, Stuttgart), to be precise under reaction conditions which are known and suitable for said reactions.

Use can be made here of variants which are known per se, but are not mentioned here in greater detail.

The axially fluorinated compounds of the formula I according to the invention can be synthesized using hydrogen fluoride under pressure or by means of amine/hydrogen fluoride adducts (for example A. V. Grosse, C. B. Linn, J. Org. Chem. 3, (1938) 26; G. A. Olah, M. Nojima, I. Kerekes, Synthesis (1973) 779); G. A. Olah, X- Y. Li, Q. Wang, G. K. S. Prakash, Synthesis (1993) 693).

The compounds according to the invention can be prepared, for example, as shown in the following reaction schemes:

Scheme 1

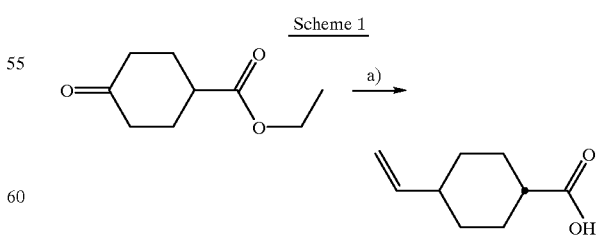

a) 1. Ph₃P = CHOMe
2. H₃O⁺
3. Ph₃P = CH₂
4. hydrolysis

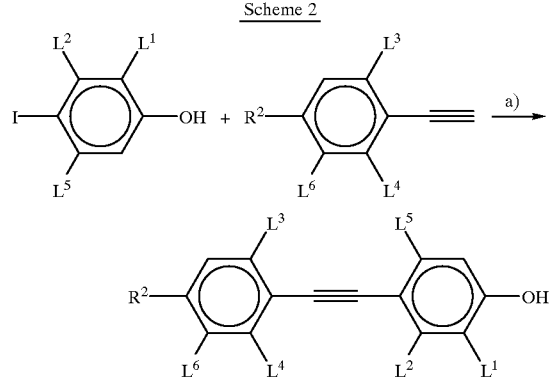
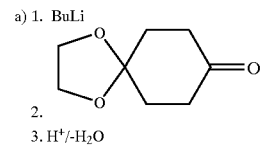
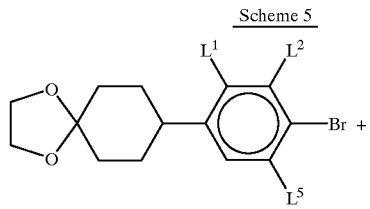
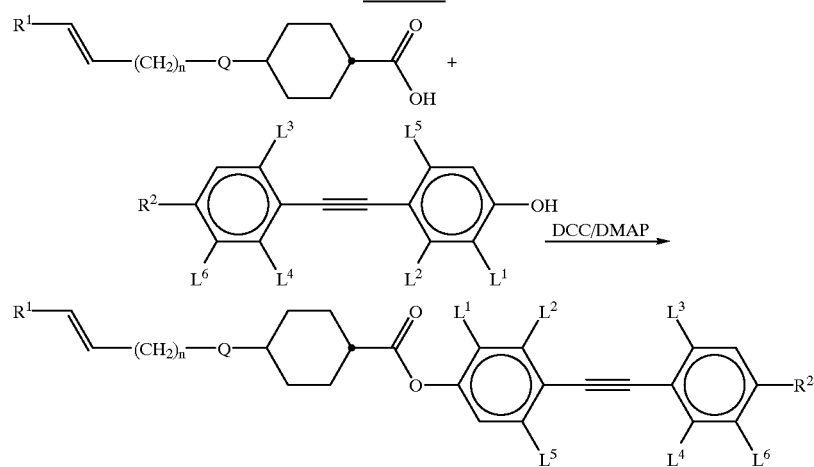
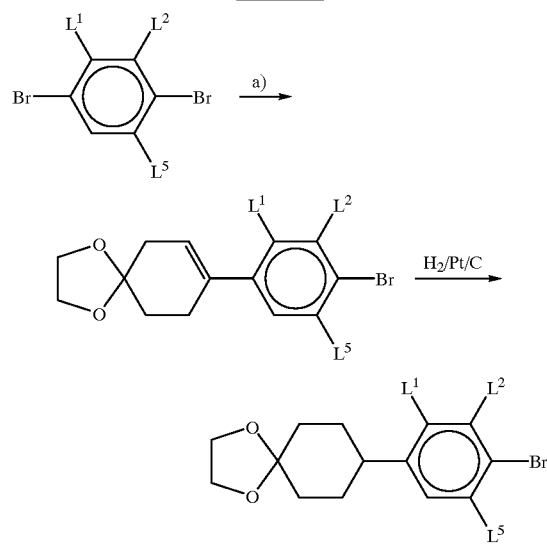
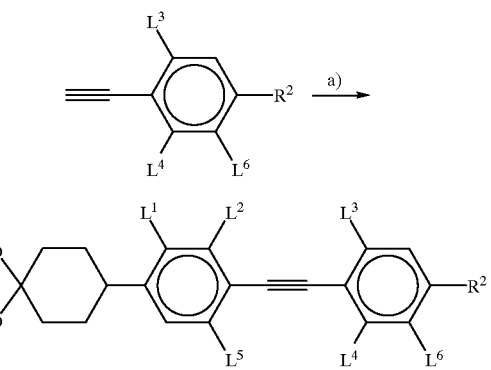

Scheme 6
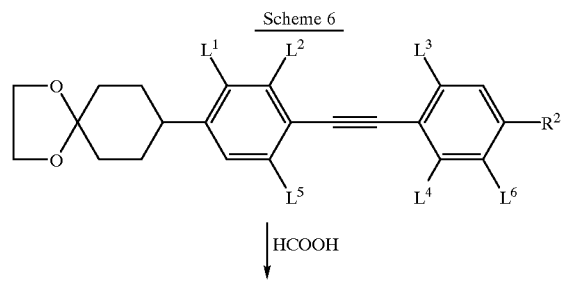
HCOOH ↓
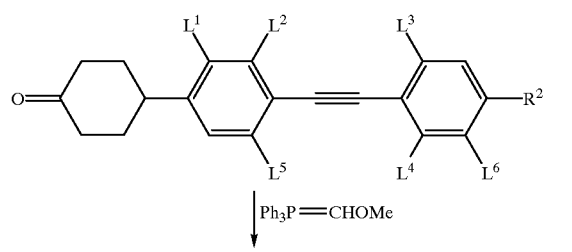
Ph₃P=CHOMe ↓
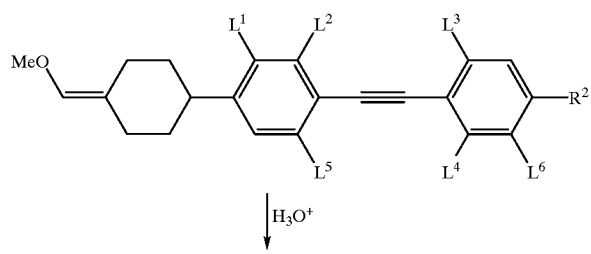
H₃O⁺ ↓
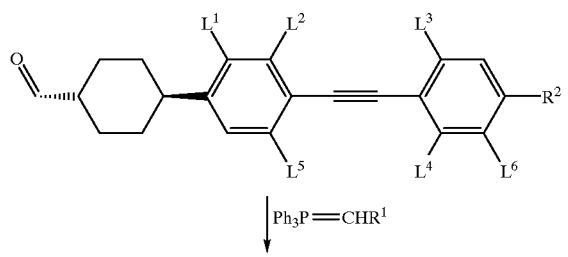
Ph₃P=CHR¹ ↓
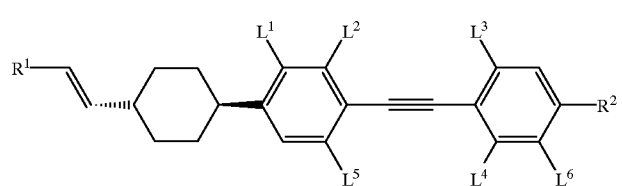

Scheme 7
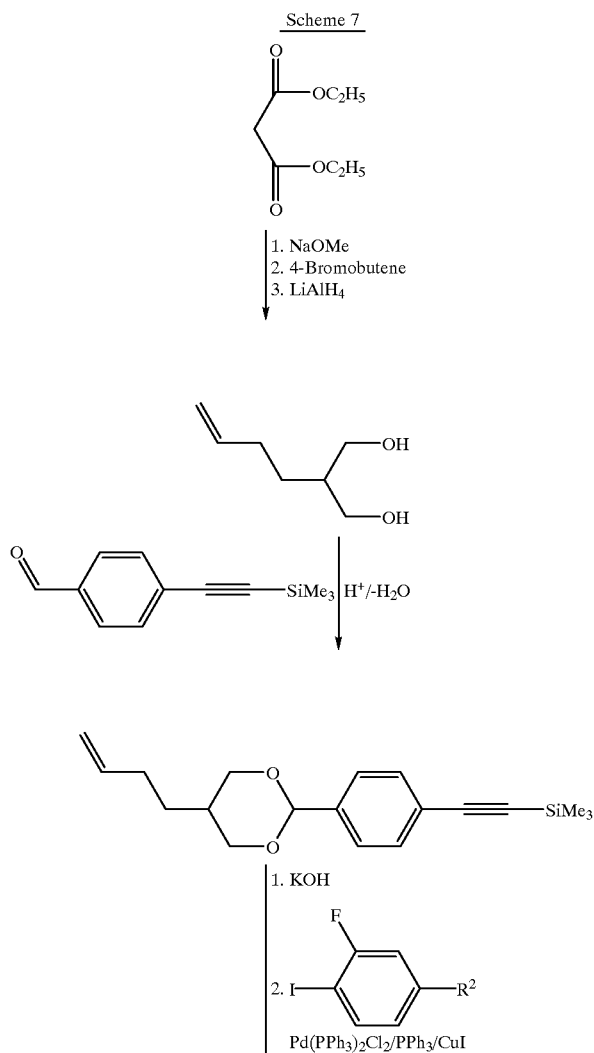
Scheme 8
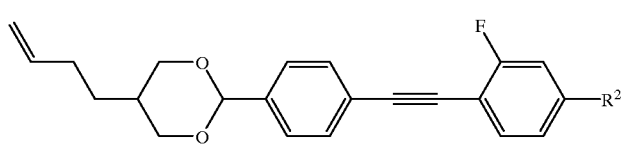
1. MeOHC=PPh₃
2. H₃O⁺
3. Cat. NaOH/MeOH (Isomerization)
4. LiAlH₄
5. MSCl
6. KI
7. PPh₃

-continued
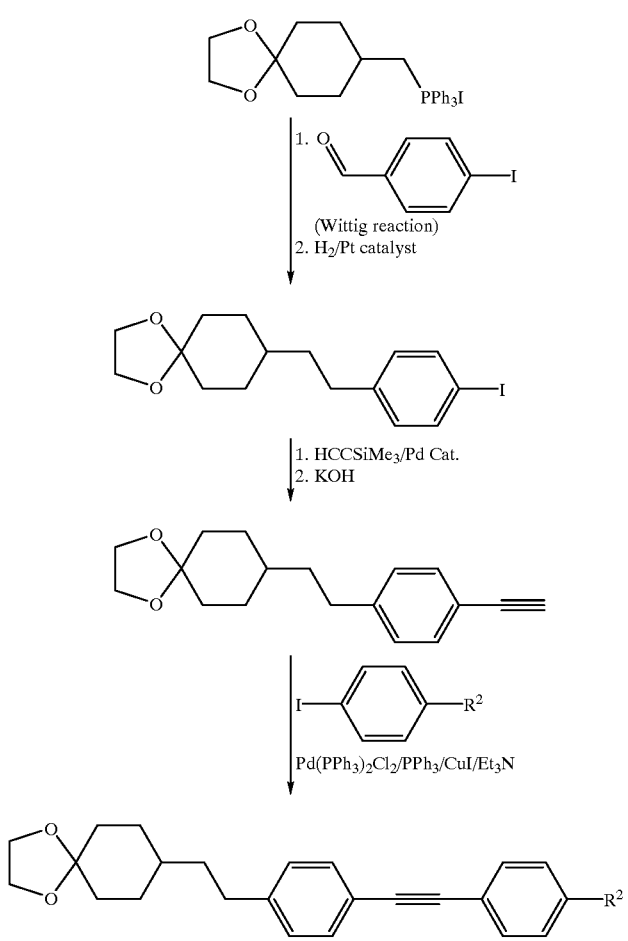
Scheme 9
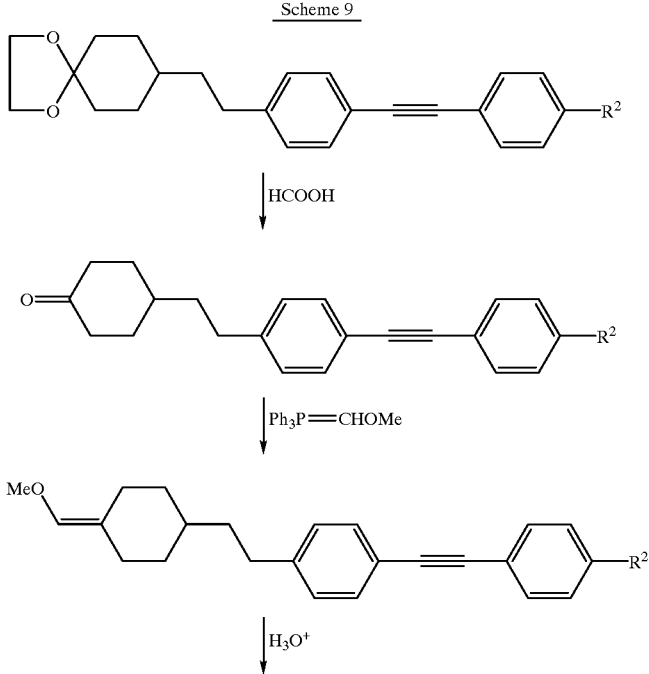

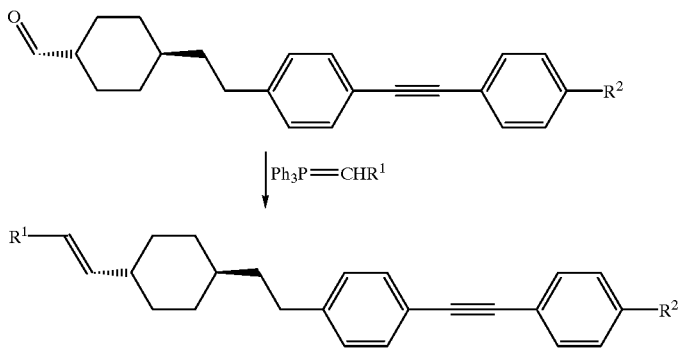

The tolans of formula I can be prepared, for example, by brominating the corresponding stilbenes and then subjecting the brominated product to dehydrohalogenation. Use can be made here of reaction variants which are known per se, but are not mentioned here in greater detail.

However, it is also possible to prepare the tolans of the formula I by using monosubstituted acetylene instead of the olefin (Synthesis 627 (1980) or Tetrahedron Lett. 27, 1171 (1986)).

Tolans of the formula I can likewise be prepared by the Fritsch-Buttenberg-Wiechell rearrangement (Ann. 279, 319, 1984), in which 1,1-diaryl-2-haloethylenes are rearranged to diarylacetylenes in the presence of strong bases.

Coupling reactions of alkynyl compounds with aryl halides to give the tolans of the formula I can be carried out analogously to the process described by A. O. King, E. Negishi, F. J. Villani and A. Silveira in J. Org. Chem 43, 358 (1978).

The tolans of the formula I are preferably prepared by reacting the corresponding aryl halides with an acetylide in a basic solvent with transition-metal catalysis. Preference is given here to palladium catalysts, in particular to a mixture of bis(triphenylphosphine)palladium(II) chloride and copper iodide in piperidine as solvent.

Esters of the formula I can also be obtained by esterification of corresponding carboxylic acids (or reactive derivatives thereof) using alcohols or phenols (or reactive derivatives thereof) or by the DCC method (DCC= dicyclohexylcarbodiimide).

The corresponding carboxylic acids and alcohols or phenols are known or can be prepared analogously to known processes.

Suitable reactive derivatives of said carboxylic acids are in particular the acid halides, especially the chlorides and bromides, furthermore the anhydrides, azides or esters, in particular alkyl esters having 1–4 carbon atoms in the alkyl group.

Suitable reactive derivatives of said alcohols or phenols are in particular the corresponding metal alkoxides or phenoxides, preferably of an alkali metal, such as Na or K.

The esterification is advantageously carried out in the presence of an inert solvent. Particularly suitable solvents are ethers, such as diethyl ether, di-n-butyl ether, THF, dioxane or anisole, ketones, such as acetone, butanone or cyclohexanone, amides, such as DMF or hexamethylphosphoric triamide, hydrocarbons, such as benzene, toluene or xylene, halogenated hydrocarbons, such as tetrachloromethane or tetrachloroethylene, and sulphoxides, such as dimethyl sulphoxide or sulpholane. Water-immiscible solvents can at the same time advantageously be used for removal by azeotropic distillation of the water formed during the esterification. It may in some cases also be possible to use an excess of an organic base, for example pyridine, quinoline or triethylamine, as solvent for the esterification. The esterification can also be carried out in the absence of a solvent, for example by simply heating the components in the presence of sodium acetate. The reaction temperature is usually between −50° and +250°, preferably between −20° and +80°. At these temperatures, the esterification reactions are generally complete after from 15 minutes to 48 hours.

In detail, the reaction conditions for the esterification depend substantially on the nature of the starting materials used. Thus, the reaction of a free carboxylic acid with a free alcohol or phenol is generally carried out in the presence of a strong acid, for example a mineral acid, such as hydrochloric acid or sulphuric acid. A preferred reaction procedure is to react an acid anhydride or, in particular, an acid chloride with an alcohol, preferably in a basic medium, important bases being, in particular, alkali metal hydroxides, such as sodium hydroxide or potassium hydroxide, alkali metal carbonates or hydrogencarbonates, such as sodium carbonate, sodium hydrogencarbonate, potassium carbonate or potassium hydrogencarbonate, alkali metal acetates, such as sodium acetate or potassium acetate, alkaline-earth metal hydroxides, such as calcium hydroxide, or organic bases, such as triethylamine, pyridine, lutidine, collidine or quinoline. A further preferred embodiment of the esterification comprises first converting the alcohol or the phenol into the sodium or potassium alkoxide or phenoxide, for example by treatment with ethanolic sodium hydroxide or potassium hydroxide solution, and isolating the product and reacting it with an acid anhydride or, in particular, acid chloride.

Nitriles can be obtained by replacement of halogens by copper cyanide or alkali metal cyanide.

In a process for the preparation of the compounds of the formula I in which Z is —CH═CH—, an aryl halide is reacted with an olefin in the presence of a tertiary amine and in the presence of a palladium catalyst (cf. R. F. Heck, Acc. Chem. Res. 12 (1979) 146). Examples of suitable aryl halides are chlorides, bromides and iodides, in particular bromides and iodides. The tertiary amines necessary for the success of the coupling reaction, such as, for example, triethylamine, are also suitable as solvent. Examples of suitable palladium catalysts are palladium salts, in particular Pd(II) acetate, with organophosphorus(III) compounds, such as, for example, triarylphosphines. The reaction can be carried out in the presence or absence of an inert solvent at temperatures between about 0° C. and 150° C., preferably between 20° C. and 100° C.; examples of suitable solvents are nitriles, such as acetonitrile, or hydrocarbons, such as benzene or toluene. The aryl halides and olefins employed as starting materials are frequently commercially available or can be prepared by methods known from the literature, for example by halogenation of corresponding parent compounds or by elimination reactions on corresponding alcohols or halides.

This method also allows the preparation of stilbene derivatives, which can be converted into the corresponding tolans of the formula I as described above. The stilbenes used as starting material for the preparation of the tolans may also be prepared by reacting a 4-substituted benzaldehyde with a corresponding phosphorus ylide by the Wittig method.

Ethers of the formula I can be obtained by etherification of corresponding hydroxyl compounds, preferably of corresponding phenols, the hydroxyl compound advantageously first being converted into a corresponding metal derivative, for example into the corresponding alkali metal alkoxide or alkali metal phenoxide, by treatment with NaH, $NaNH_2$, NaOH, KOH, $Na_2CO_3$ or $K_2CO_3$. This metal derivative can then be reacted with the appropriate alkyl halide, alkyl sulphonate or dialkyl sulphate, advantageously in an inert solvent, such as, for example, acetone, 1,2-dimethoxyethane, DMF or dimethyl sulphoxide or alternatively with an excess of aqueous or aqueous-alcoholic NaOH or KOH, at temperatures between about 20° C. and 100° C.

In order to prepare the laterally substituted fluorine or chlorine compounds of the formula I, corresponding analine derivatives can be reacted with sodium nitrite and either with tetrafluoroboric acid (in order to introduce an F atom) or with copper (I) chloride (in order to introduce a Cl atom) to give the diazonium salts, which are then thermally decomposed at temperatures of 100–140° C.

The linking of an aromatic ring to a nonaromatic ring or of two nonaromatic rings is preferably obtained by condensation of an organolithium or organomagnesium compound with a ketone if the two rings are separated by an aliphatic group Z.

The organometallic compounds are prepared, for example, by metal-halogen exchange (for example in accordance with Org. React. 6, 339–366 (1951)) between the corresponding halogen compound and an organolithium compound, such as, preferably, tert-butyl lithium or lithium naphthaleneide, or by reaction with magnesium turnings.

The linking of two aromatic rings or of an aliphatic group Z with an aromatic ring is preferably carried out by Friedel-Crafts alkylation or acylation by reacting the corresponding aromatic compounds with catalysis by a Lewis acid. Suitable Lewis acids are, for example, $SnCl_4$, $ZnCl_2$ or, in particular, $AlCl_3$ and $TiCl_4$.

Aromatic compounds can furthermore be coupled by reacting aryl halides with aryltin compounds. These reactions are preferably carried out with addition of a catalyst, such as, for example, a palladium(0) complex, in inert solvents, such as hydrocarbons, at high temperatures, for example in boiling xylene, under a protective gas.

The linking of two aromatic rings can furthermore be carried out by the Ullmann reaction (for example Synthesis 1974, 9) between aryl iodides and copper iodide, but preferably between an arylcopper compound and an aryl iodide, or by the Gomberg-Bachmann reaction between an aryldiazonium salt and the corresponding aromatic compound (for example Org. React. 2, 224 (1944)).

Furthermore, the compounds of the formula I can be prepared by reducing a compound which contains one or more reducible groups including unsaturated carbon to carbon bonds in place of H atoms, but otherwise conforms to the formula I.

Suitable reducible groups are preferably carbonyl groups, in particular keto groups, furthermore, for example, free or esterified hydroxyl groups or aromatically bonded halogen atoms. Preferred starting materials for the reduction are compounds which conform to the formula I, but contain a cyclohexene ring or cyclohexanone ring in place of a cyclohexane ring and/or contain a —CH=CH— group in place of a —CH$_2$CH$_2$— group and/or contain a —CO— group in place of a —CH$_2$— group and/or contain a free or functionally derived (for example in the form of its p-toluenesulphonate) OH group in place of an H atom.

The reduction can be carried out, for example, by catalytic hydrogenation at temperatures between about 0° and about 200° and at pressures between about 1 and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Suitable catalysts are expediently noble metals, such as Pt or Pd, which may be employed in the form of oxides (for example $PtO_2$ or PdO), on a support (for example Pd on charcoal, calcium carbonate or strontium carbonate) or in finely divided form.

Ketones can also be reduced by the methods of Clemmensen (using zinc, zinc amalgam or tin and hydrochloric acid, expediently in aqueous-alcoholic solution or in the heterogeneous phase with water/toluene at temperatures between about 80 and 120°) or Wolff-Kishner (using hydrazine, expediently in the presence of alkali, such as KOH or NaOH, in a high-boiling solvent, such as diethylene glycol or triethylene glycol, at temperatures between about 100 and 2000) to give the corresponding compounds of the formula I which contain alkyl groups and/or —CH$_2$CH$_2$— bridges.

Furthermore, reductions using complex hydrides are possible. For example, arylsulphonyloxy groups can be removed reductively using $LiAlH_4$, in particular p-toluenesulphonyloxymethyl groups can be reduced to methyl groups, expediently in an inert solvent, such as diethyl ether or THF, at temperatures between about 0 and 100°. Double bonds can be hydrogenated using tributyltin hydride in methanol.

The novel liquid-crystalline media preferably comprise 2 to 40, in particular 4 to 30, components as further constituents besides one or more novel compounds. These media very particularly preferably comprise 7 to 25 components besides one or more novel compounds. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes optionally halogenated stilbenes, benzyl phenyl ethers, tolans and substituted cinnamic acids. The 1,4-phenylene groups in these compounds may also be fluorinated.

The most important compounds suitable as further constituents of novel media can be characterized by the formulae 1, 2, 3, 4 and 5:

$$R'-L-E-R'' \qquad \qquad 1$$

$$R'-L-COO-E-R'' \qquad \qquad 2$$

$$R'-L-OOC-E-R'' \qquad \qquad 3$$

$$R'-L-CH_2CH_2-E-R'' \qquad \qquad 4$$

$$R'-L-C\equiv C-E-R'' \qquad \qquad 5$$

In the formulae 1, 2, 3, 4 and 5, L and E, which may be identical or different, are in each case, independently of one another, a bivalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

In the formulae 1, 2, 3, 4 and 5, R', independently of one another, is alkyl, alkenyl, alkoxy, alkoxyalkyl, alkenyloxy or alkanoyloxy having up to 8 carbon atoms. R", independently of one another, is alkyl, alkenyl, alkoxy, alkoxyalkyl, alkenyloxy or alkanoyloxy having up to 8 carbon atoms, F, Cl, CN, NCS or $-(O)_iCH_{3-(k+1)}F_kCl_1$, where i is 0 or 1, and r and s are 1, 2 or 3.

One of the radicals L and E is preferably Cyc, Phe or Pyr. E is preferably Cyc, Phe or Phe-Cyc. The novel media preferably comprise one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, -G-Phe- and -G-Cyc-.

In a smaller sub-group of the compounds of the formulae 1, 2, 3, 4 and 5, R' and R" are in each case, independently of one another, alkyl, alkenyl, alkoxy, alkoxyalkyl, alkenyloxy or alkanoyloxy having up to 8 carbon atoms. This smaller sub-group is called group A below, and the compounds are denoted by the sub-formulae 1a, 2a, 3a, 4a and 5a. In most of these compounds, R' and R" are different from one another, one of these radicals usually being alkyl, alkenyl, alkoxy or alkoxy-alkyl.

In another smaller sub-group of the compounds of the formulae 1, 2, 3, 4 and 5 which is known as group B, R" is —F, —Cl, —NCS or $-(O)_iCH_{3-(k+1)}F_kCl_1$, where i is 0 or 1, and k and 1 are 1, 2 or 3; the compounds in which R" has this meaning are denoted by the sub-formulae 1b, 2b, 3b, 4b and 5b. Particular preference is given to those compounds of the sub-formulae 1b, 2b, 3b, 4b and 5b in which R" is —F, —Cl, —NCS, —CF$_3$, —OCHF$_2$ or —OCF$_3$.

In the compounds of the sub-formulae 1b, 2b, 3b, 4b and 5b, R' is as defined for the compounds of the sub-formulae 1a–5a and is preferably alkyl, alkenyl, alkoxy or alkoxyalkyl.

In a further smaller sub-group of the compounds of the formulae 1, 2, 3, 4 and 5, R" is —CN; this sub-group is known as group C below, and the compounds of this sub-group are correspondingly described by sub-formulae 1c, 2c, 3c, 4c and 5c. In the compounds of the sub-formulae 1c, 2c, 3c, 4c and 5c, R' is as defined for the compounds of the sub-formulae 1a–5a and is preferably alkyl, alkoxy or alkenyl.

In addition to the preferred compounds of groups A, B and C, other compounds of the formulae 1, 2, 3, 4 and 5 having other variants of the proposed substituents are also customary. All these substances can be obtained by methods which are known from the literature or analogously thereto.

Besides novel compounds of the formula I, the novel media preferably comprise one or more compounds selected from group A and/or group B and/or group C. The proportions by weight of the compounds from these groups in the novel media are preferably:

Group A: 0 to 90%, preferably 20 to 90%, in particular 30 to 90%

Group B: 0 to 80%, preferably 10 to 80%, in particular 10 to 65%

Group C: 0 to 80%, preferably 5 to 80%, in particular 5 to 50%, the sum of the proportions by weight of the group A and/or B and/or C compounds present in the particular novel media preferably being 5%–90% and in particular 10% to 90%.

The novel media preferably comprise 1 to 40%, particularly preferably 5 to 30%, of the novel compounds. Further preferred media are those which comprise more than 40%, in particular 45 to 90%, of novel compounds. The media preferably comprise three, four or five novel compounds.

The novel media are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of colored guest-host systems, or substances can be added to modify the dielectric anisotropy, the viscosity and/or the orientation of the nematic phases.

The entire disclosure of all applications, patents and publications, cited above, and of corresponding German application No. 198 271 29.8, filed Jun. 18, 1998 is hereby incorporated by reference.

EXAMPLES

The examples below are intended to illustrate the invention without representing a limitation. Above and below, percent data are percent by weight. All temperatures are given in degrees Celsius. M.p.=melting point, cl.p.=clearing point. Furthermore, C=crystalline state, N=nematic phase, Sm=smectic phase and I=isotropic phase. The numbers between these symbols indicate the conversion temperatures. An denotes optical anisotropy (589 nm, 20° C.) and As dielectric anisotropy (1kHz, 20° C.). The viscosity (mm$^2$/sec) was determined at 20° C.

"Conventional work-up" means that water is added if necessary, the mixture is extracted with dichloromethane, diethyl ether or toluene, the organic phase is separated off, dried and evaporated, and the product is purified by distillation under reduced pressure or crystallization and/or chromatography.

The following abbreviations are used:
THF tetrahydrofuran
KOtBu potassium tert-butoxide
RT room temperature
MTB ether methyl tert-butyl ether
DCC dicyclohexylcarbodiimide

Example 1

Under a nitrogen atmosphere, 425.5 g of ethyl 4-cyclohexanecarboxylate and 856.7 g of methoxymethyltriphenylphosphonium chloride were suspended in 2.2 l of methyl tert-butyl ether. A solution of 280.4 g of potassium tert-butoxide in 400 ml of tetrahydrofuran was then added dropwise to the stirred suspension. The suspension was then stirred overnight at RT, and the next day 430 ml of 10% hydrochloric acid were added and the mixture was warmed at 55° C. for 1 hour. 50 ml of water were then added to the suspension. Conventional work-up gave ethyl 4-formylcyclohexanecarboxylate.

Example 2

240 g of ethyl 4-formylcyclohexanecarboxylate were dissolved in 2.4 l of THF at 10–15° C. under nitrogen, and 531 g of ethyltriphenylphosphonium bromide were added. 160 g of potassium tert-butoxide were introduced in portions into the resultant suspension over a period of 1.5 hours, the temperature being held at below 20° C. After the mixture had been stirred overnight, the mixture was hydrolyzed using water the next day and rendered slightly acidic using 2 N HCl. Conventional work-up gave ethyl 4-propenylcyclohexanecarboxylate as an E/Z isomer mixture.

Ethyl 4-vinylcyclohexanecarboxylate can be prepared analogously using methyltriphenylphosphonium bromide.

Example 3

170 g of ethyl 4-propenylcyclohexanecarboxylate from Example 2, 38 g of sodium hydroxide, 215 ml of water and 1075 ml of ethanol were combined and stirred overnight at RT. Conventional work-up gave 4-propenylcyclohexanecarboxylic acid as an E/Z isomer mixture.

4-Vinylcyclohexanecarboxylic acid can be prepared analogously.

Example 4

120 g of 4-propenylcyclohexanecarboxylic acid from Example 3, 31.2 g of sodium benzenesulphinate, 285 ml of 1 N HCl, 1 l of toluene and 500 ml of THF were combined and refluxed for 2 days. The aqueous phase was then removed, and a further 31.2 g of sodium benzenesulphinate and 285 ml of 1 N HCl were added. After the reaction mixture had been refluxed for 2.5 hours, the aqueous phase was again removed, 31.2 g of sodium benzenesulphinate and 285 ml of 1 N HCl were added, and the mixture was refluxed for 3 hours. Conventional work-up gave 4-E-propenylcyclohexanecarboxylic acid in the form of a colorless solid.

Example 5

50 g of 4-ethynyltoluene, 94.6 g of 4-iodophenol and 250 ml of triethylamine were mixed at RT under a nitrogen atmosphere, and 0.35 g of triphenylphosphine and 0.2 g of copper iodide were added. 0.25 g of bis(triphenylphosphine)palladium(II) chloride were then introduced with stirring. After 30 minutes, a further 0.25 g of bis(triphenylphosphine)palladium(II) chloride and after a further 15 minutes a further 0.25 g of bis(triphenylphosphine)palladium(II) chloride were introduced, during which the temperature was held at between 40 and 55° C. After the reaction mixture had been stirred overnight, it was poured into conc. HCl/ice and subjected to conventional work-up, giving 4-p-tolylethynylphenol in the form of a solid.

Example 6

5.0 g of 4-vinylcyclohexanecarboxylic acid, 6.7 g of 4-p-tolylethynylphenol, 4.0 g of 4-(dimethylamino)pyridine and 250 ml of toluene were mixed at RT, 7.3 g of DCC in 50 ml of toluene were added, and the mixture was stirred vigorously overnight at RT, during which the urea formed precipitated. 1 g of oxalic acid was then added, and the mixture was stirred at RT for a further hour in order to destroy the excess DCC. The conventional work-up gave 4-p-tolylethynylphenyl 4-vinylcyclohexanecarboxylate in the form of colorless crystals.

Example 7

25.0 g of p-tolylacetylene and 12.71 g of tetrakis(triphenylphosphine)palladium(0) (9.2% of Pd) were introduced into 500 ml of pyrrolidine, and 65.36 g of [4-(4-bromophenyl)cyclohexyl]methanol were added quickly. The mixture was then warmed at 80° C. for 2.5 hours with stirring, cooled and subjected to conventional work-up, giving [4-(4-p-tolylethynylphenyl)cyclohexyl]methanol as a crystalline solid.

Example 8

36.6 g of [4-(4-p-tolylethynylphenyl)cyclohexyl]methanol were mixed with 300 ml of dichloromethane, and a mixture of 21 g of Celite and 28.5 g of pyridinium chlorochromate (PCC) were added under a nitrogen atmosphere. The reaction mixture was stirred overnight at RT. 100 ml of isopropanol were then added to the black suspension, and the mixture was stirred at RT for 1½ hours in order to destroy the excess PCC. This suspension was then filtered, and the filtrate was subjected to conventional work-up, giving 4-(4-p-tolylethynylphenyl)cyclohexanecarbaldehyde in the form of a colorless solid.

Example 9

14.03 g of 4-(4-p-tolylethynylphenyl)cyclohexanecarbaldehyde were dissolved in 100 ml of THF, and 15.22 g of ethyltriphenylphosphonium bromide were added quickly under a nitrogen atmosphere. 4.6 g of potassium tert-butoxide were then added in portions. The suspension was stirred overnight at RT, then poured into water and neutralized using 2 N hydrochloric acid solution. Conventional work-up gave 1-propenyl-4-(4-p-tolylethynylphenyl)cyclohexane as an E/Z isomer mixture.

Example 10

26.0 g of 1-propenyl-4-(4-p-tolylethynylphenyl)cyclohexane from Example 9, 10.34 g of sodium benzenesulphinate, 100 ml of 2 N hydrochloric acid solution, 175 ml of toluene and 87 ml of THF were combined and heated to reflux. After 4 hours, the reaction mixture was allowed to cool, and the aqueous phase was removed. A further 10.34 g of sodium benzenesulphinate and 100 ml of 2 N hydrochloric acid solution were then added, and the mixture was refluxed for a further 2 hours, the aqueous phase was again removed after cooling, and a further 10.34 g of sodium benzenesulphinate and 100 ml of 2 N hydrochloric acid solution were added, the mixture was refluxed overnight, and subsequently subjected to conventional work-up, giving 1-E-propenyl-4-(4-p-tolylethynylphenyl)cyclohexane in the form of a colourless solid.

The following compounds according to the invention are obtained analogously using the corresponding precursors.

Examples 11–18

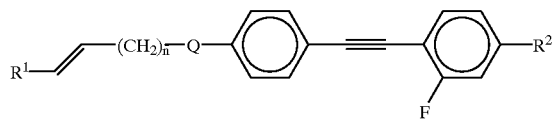

| | n | $R^1$ | Q | $R^2$ |
|---|---|---|---|---|
| (11) | 0 | H | — | $CH=CH_2$ |
| (12) | 0 | Methyl | — | $E-CH_2CH=CHCH_3$ |
| (13) | 0 | H | — | $OCH_2CH=CH_2$ |
| (14) | 2 | H | — | $OCF_3$ |
| (15) | 2 | Methyl | — | F |
| (16) | 0 | H | —O— | $CH=CH_2$ |
| (17) | 0 | Methyl | —O— | $E-CH=CHCH_3$ |
| (18) | 2 | H | —O— | F |

Examples 19–28

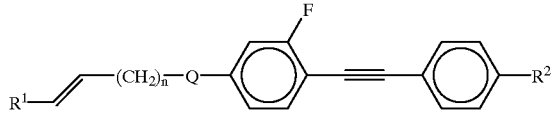

| | n | $R^1$ | Q | $R^2$ |
|---|---|---|---|---|
| (19) | 0 | H | — | $OCF_3$ |
| (20) | 0 | Ethyl | —O— | F |

-continued

| | n | $R^1$ | Q | $R^2$ |
|---|---|---|---|---|
| (21) | 0 | H | — | $OCHF_2$ |
| (22) | 2 | H | — | $OCHF_2CF_3$ |
| (23) | 2 | Methyl | — | $OCF_3$ |
| (24) | 0 | H | —O— | $E-CH_2CH=CHCH_3$ |
| (25) | 0 | H | — | $CH=CH_2$ |
| (26) | 0 | Methyl | — | $E-CH=CHCH_3$ |
| (27) | 2 | H | —O— | $CH_2CH_2CH=CH_2$ |
| (28) | 2 | Ethyl | —O— | $—OCH_2CH=CH_2$ |

Examples 29–38

(structure: $R^1$—CH=CH—$(CH_2)_n$—Q—[phenyl-3-F]—C≡C—[phenyl]—$R^2$)

| | n | $R^1$ | Q | $R^2$ |
|---|---|---|---|---|
| (29) | 0 | H | — | $OCF_3$ |
| (30) | 0 | Methyl | —O— | F |
| (31) | 0 | H | — | $OCHF_2$ |
| (32) | 2 | H | —O— | $OCHF_2CF_3$ |
| (33) | 2 | Methyl | — | $OCF_3$ |
| (34) | 0 | H | — | $E-OCH_2CH=CHCH_3$ |
| (35) | 0 | Ethyl | — | $CH=CH_2$ |
| (36) | 0 | H | — | $E-CH=CHCH_3$ |
| (37) | 2 | H | —O— | $CH_2CH_2CH=CH_2$ |
| (38) | 2 | Methyl | —O— | $—OCH_2CH=CH_2$ |

Examples 39–55

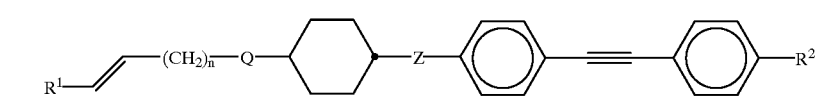

| | n | $R^1$ | Q | Z | $R^2$ |
|---|---|---|---|---|---|
| (39) | 0 | H | — | — | $OCF_3$ |
| (40) | 0 | Ethyl | —O— | — | F |
| (41) | 0 | H | — | —COO— | Ethyl C 89 N 211 I $\Delta n$ 0.228 $\Delta\epsilon$ 2.04 |
| (42) | 0 | H | — | —COO— | Methyl C 115 N 214 I $\Delta n$ 0.223 $\Delta\epsilon$ 0.75 |
| (43) | 2 | Methyl | — | — | O methyl |
| (44) | 0 | H | —O— | —COO— | O-n-Propyl |
| (45) | 0 | Methyl | — | —COO— | Ethyl C 96 N 245 I $\Delta n$ 0.226, $\Delta\epsilon$ 0.22 |
| (46) | 0 | Methyl | — | —COO— | Methyl C 116 N 259 I $\Delta n$ 0.228 $\Delta\epsilon$ −0.18 |

-continued

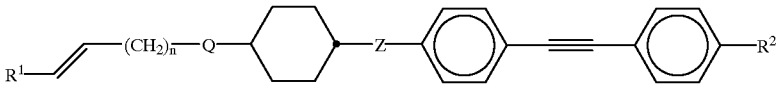

| | n | R¹ | Q | Z | R² |
|---|---|---|---|---|---|
| (47) | 2 | H | —O— | — | CH₂CH₂CH=CH₂ |
| (48) | 2 | Ethyl | —O— | —CH₂CH₂— | —OCH₂CH=CH₂ |
| (49) | 0 | H | — | — | Methyl C 123 N 197 I |
| | | | | | Δn 0.265 |
| | | | | | Δε 1.56 |
| (50) | 0 | Methyl | — | — | Methyl C 158 N 244I |
| | | | | | Δn 0.255 |
| | | | | | Δε 0.93 |
| (51) | 2 | Methyl | — | — | Ethyl |
| (52) | 1 | H | —O— | — | O—Methyl |
| (53) | 2 | H | —O— | —COO— | —OCH₂CH=CH₂ |
| (54) | 0 | H | — | —CH=CH— | Methyl |
| (55) | 0 | H | — | —CH=CH— | CH=CH₂ |

Examples 56–71

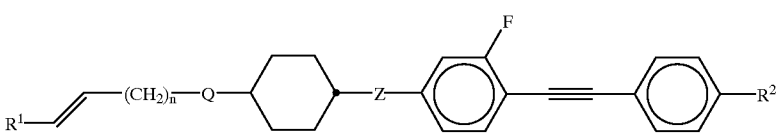

| | n | R¹ | Q | Z | R² |
|---|---|---|---|---|---|
| (56) | 0 | H | — | — | OCF₃ |
| (57) | 0 | Methyl | — | —COO— | F |
| (58) | 0 | H | —O— | —COO— | Ethyl |
| (59) | 2 | H | — | —COO— | Methyl |
| (60) | 2 | Ethyl | —O— | —CH₂CH₂— | O—methyl |
| (61) | 0 | H | — | — | O-n-propyl |
| (62) | 0 | Methyl | — | — | Pentyl |
| (63) | 0 | H | — | —COO— | E-CH=CHCH₃ |
| (64) | 2 | H | — | — | CH₂CH₂CH=CH₂ |
| (65) | 2 | Ethyl | — | —COO— | OCH₂CH=CH₂ |
| (66) | 0 | H | —O— | — | O-n-propyl |
| (67) | 0 | H | —O— | —COO— | O-n-propyl |
| (68) | 1 | H | — | — | n-Butyl |
| (69) | 2 | H | — | — | n-Pentyl |
| (70) | 0 | Methyl | —O— | —CH=CH— | Methyl |
| (71) | 0 | H | — | —CH=CH— | CH=CH₂ |

Examples 72–82

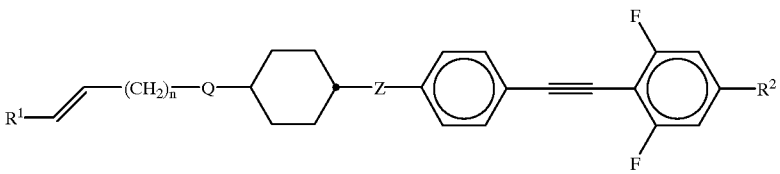

| | n | R¹ | Q | Z | R² |
|---|---|---|---|---|---|
| (72) | 0 | H | — | — | Ethyl |
| (73) | 0 | Methyl | — | —COO— | Methyl |
| (74) | 0 | H | —O— | —COO— | O—methyl |
| (75) | 2 | H | — | —COO— | n-Pentyl |
| (76) | 2 | Ethyl | —O— | —CH₂CH₂— | O-n-propyl |

-continued

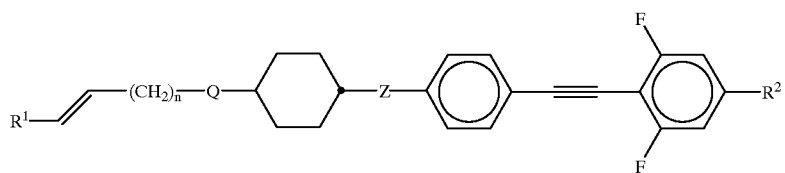

| | n | R¹ | Q | Z | R² |
|---|---|---|---|---|---|
| (77) | 0 | H | — | — | n-Butyl |
| (78) | 0 | Methyl | — | — | CH=CH₂ |
| (79) | 0 | H | — | —COO— | E-CH=CHCH₃ |
| (80) | 2 | H | — | — | CH₂CH₂CH=CH₂ |
| (81) | 2 | Ethyl | — | —COO— | —OCH₂CH=CH₂ |
| (82) | 0 | H | — | —CH=CH— | Methyl |

Examples 83–102

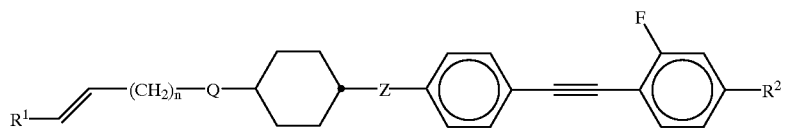

| | n | R¹ | Q | Z | R² |
|---|---|---|---|---|---|
| (83) | 0 | H | — | — | OCF₃ |
| (84) | 0 | Methyl | — | —COO— | F |
| (85) | 0 | H | —O— | —COO— | —OCH=CH₂ |
| (86) | 2 | H | — | —COO— | CH=CH₂ |
| (87) | 2 | Ethyl | —O— | —CH₂CH₂— | Methyl |
| (88) | 0 | H | — | — | Methyl |
| (89) | 0 | Methyl | — | — | Ethyl |
| (90) | 0 | H | — | —COO— | O—methyl |
| (91) | 2 | H | — | — | CH₂CH₂CH=CH₂ |
| (92) | 2 | Ethyl | — | —COO— | OCH₂CH=CH₂ |
| (93) | 0 | H | — | —COO— | Methyl C 113 N 198 I Δn 0.228 Δε 1.32 |
| (94) | 0 | Methyl | — | —COO— | Methyl C 112 N 245 I Δn 0.223 Δε 2.05 |
| (95) | 1 | Ethyl | —O— | — | n-Propyl |
| (96) | 2 | Ethyl | —O— | — | n-Butyl |
| (97) | 0 | Methyl | —O— | —COO— | n-Pentyl |
| (98) | 0 | Methyl | —O— | —CH₂CH₂— | O-n-propyl |
| (99) | 0 | H | —O— | — | O-n-propyl |
| (100) | 0 | H | —O— | —COO— | O-n-propyl |
| (101) | 0 | H | — | —CH=CH— | Methyl |
| (102) | 0 | H | — | —CH=CH— | CH=CH₂ |

Examples 103–114

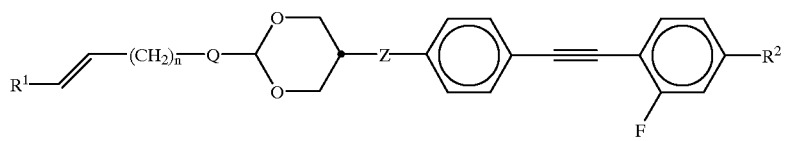

| | n | R¹ | Q | Z | R² |
|---|---|---|---|---|---|
| (103) | 0 | H | — | — | Methyl |
| (104) | 0 | Methyl | — | —COO— | Ethyl |

-continued

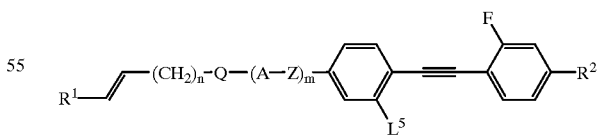

| | n | R¹ | Q | Z | R² |
|---|---|---|---|---|---|
| (105) | 0 | H | —O— | —COO— | n-Propyl |
| (106) | 2 | H | — | —COO— | n-Pentyl |
| (107) | 2 | Ethyl | —O— | —CH₂CH₂— | n-propyl |
| (108) | 0 | H | — | — | E-CH₂CH₂=CHCH₃ |
| (109) | 0 | Methyl | — | — | CH=CH₂ |
| (110) | 0 | H | — | —COO— | E-CH=CHCH₃ |
| (111) | 2 | H | — | — | CH₂CH₂CH=CH₂ |
| (112) | 2 | Ethyl | — | —COO— | OCH₂CH=CH₂ |
| (113) | 0 | H | — | —CH=CH— | Methyl |
| (114) | 0 | H | — | —CH=CH— | OCH₂CH=CH₂ |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A tolan compound of the formula

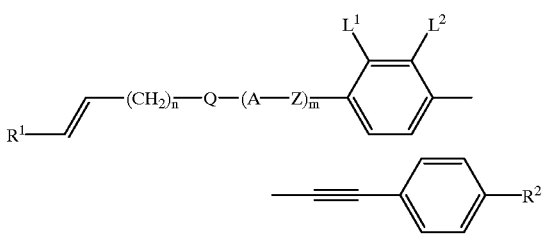

in which

R¹ is H or an alkyl radical having 1–12 carbon atoms which is unsubstituted, monosubstituted by CN or CF, or monosubstituted to perhalosubstituted by halogen, where one or more non-adjacent CH₂ groups in these radicals are, independently of one another, each optionally replaced by —CH=CH—, —O—, —S—, —CO—,

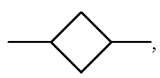

—CO—O—, —O—CO—, or —O—CO—O—,

R² is alkyl or alkoxy having 1 to 10 carbon atoms which is unsubstituted or monosubstituted to perhalosubstituted by halogen; alkenyl or alkenyloxy having 2 to 10 carbon atoms which is unsubstituted or at least monosubstituted by —CN, CF₃ or —F; or —F, —Cl, —CF₃, —OCHF₂, —OCF₃, —OCHFCF₃ or —OCF₂CF₃, L¹ is either H or F, Q is —O— or a single bond A are independently a trans-1,4-cyclohexylene radical, in which one or more non-adjacent CH₂ groups are optionally replaced by —O— and/or —S—; or a 1,4-cyclohexenylene radical where the rings are optionally substituted by CN, Cl or F, Z are, independently of one another, —CO—O—, —O—CO—, —CH₂O—, —O—, —O—CH₂—, —CH₂CH₂—, —CH=CH—, —C≡C— or a single bond, n is 0, 1, 2, 3 or 4 and m is 0, 1 or 2, with the proviso that compounds in which m is 0 and simultaneously R² is alkyl or alkoxy are excluded.

2. A tolan compound as claimed in claim 1, wherein R¹ is H, straight chain alkyl having 1 to 10 carbon atoms, alkenyl having 2 to 10 carbon atoms, or alkoxy having from 1 to 10 carbon atoms.

3. A tolan compound as claimed in claim 1, wherein R² is F, OCF₃, straight chain alkyl or alkoxy having 1 to 10 carbon atoms, or alkenyl or alkenyloxy having 2 to 10 carbon atoms.

4. A tolan compound as claimed in claim 1, wherein Z is —CH₂CH₂—, —COO—, or a single bond.

5. A tolan compound as claimed in claim 1, wherein m is 1 or 0.

6. A tolan compound as claimed in claim 1, wherein A is

7. A tolan compound of the formula

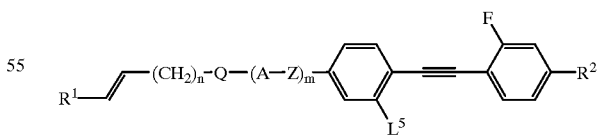

in which

R¹ is H or an alkyl radical having 1–12 carbon atoms which is unsubstituted, monosubstituted by CN or CF, or monosubstituted to perhalosubstituted by halogen, where one or more non-adjacent CH₂ groups in these radicals are, independently of one another, each optionally replaced by —CH=CH—, —O—, —S—, —CO—,

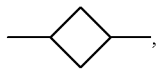

—CO—O—, —O—CO—, or —O—CO—O—, $R^2$ is alkyl or alkoxy having 1 to 10 carbon atoms which is unsubstituted or monosubstituted to perhalosubstituted by halogen; alkenyl or alkenyloxy having 2 to 10 carbon atoms which is unsubstituted or at least monosubstituted by —CN, $CF_3$ or —F; or —F, —Cl, —$CF_3$, —$OCHF_2$, —$OCF_3$, —$OCHFCF_3$ or —$OCF_2CF_3$, $L^5$ is either H or F, Q is —O— or a single bond A are independently a trans-1,4-cyclohexylene radical, in which one or more non-adjacent $CH_2$ groups are optionally replaced by —O— and/or —S—; or a 1,4-cyclohexenylene radical where the rings are optionally substituted by CN, Cl or F, Z are, independently of one another, —CO—O—, —O—CO—, —$CH_2O$—, —O—, —O—$CH_2$—, —$CH_2CH_2$—, —CH=CH—, —C≡C— or a single bond, n is 0, 1, 2, 3 or 4 and m is 0, 1 or 2, with the proviso that compounds in which m is 0 and simultaneously $R^2$ is alkyl or alkoxy are excluded.

8. A tolan compound as claimed in claim 7, wherein $R^1$ is H, straight chain alkyl having 1 to 10 carbon atoms, alkenyl having 2 to 10 carbon atoms, or alkoxy having from 1 to 10 carbon atoms.

9. A tolan compound as claimed in claim 7, wherein $R^2$ is F, $OCF_3$, straight chain alkyl or alkoxy having 1 to 10 carbon atoms, or alkenyl or alkenyloxy having 2 to 10 carbon atoms.

10. A tolan compound as claimed in claim 7, wherein Z is —$CH_2CH_2$—, —COO—, or a single bond.

11. A tolan compound as claimed in claim 7, wherein m is 1 or 0.

12. A tolan compound as claimed in claim 7, wherein A is

13. A tolane compound according to the following formula:

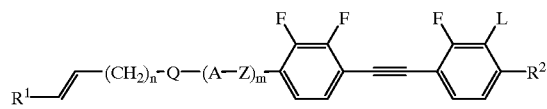

in which $R^1$ is H or an alkyl radical having 1–12 carbon atoms which is unsubstituted, monosubstituted by CN or CF, or monosubstituted to perhalosubstituted by halogen, where one or more non-adjacent $CH_2$ groups in these radicals are, independently of one another, each optionally replaced by —CH=CH—, —O—, —S—, —CO—,

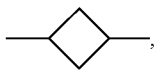

—CO—O—, —O—CO—, or —O—CO—O—, $R^2$ is alkyl or alkoxy having 1 to 10 carbon atoms which is unsubstituted or monosubstituted to perhalosubstituted by halogen; alkenyl or alkenyloxy having 2 to 10 carbon atoms which is unsubstituted or at least monosubstituted by —CN, $CF_3$ or —F; or —F, —Cl, —$CF_3$, —$OCHF_2$, —$OCF_3$, —$OCHFCF_3$ or —$OCF_2CF_3$, L is either H or F, Q is —O— or a single bond A are independently a trans-1,4-cyclohexylene radical, in which one or more non-adjacent $CH_2$ groups are optionally replaced by —O— and/or —S—; or a 1,4-cyclohexenylene radical where the rings are optionally substituted by CN, Cl or F, Z are, independently of one another, —CO—O—, —O—CO—, —$CH_2O$—, —O—, —O—$CH_2$—, —$CH_2CH_2$—, —CH=CH—, —C≡C— or a single bond, n is 0, 1, 2, 3 or 4 and m is 0, 1 or 2, with the proviso that compounds in which m is 0 and simultaneously $R^2$ is alkyl or alkoxy are excluded.

14. A tolan compound as claimed in claim 13, wherein $R^1$ is H, straight chain alkyl having 1 to 10 carbon atoms, alkenyl having 2 to 10 carbon atoms, or alkoxy having from 1 to 10 carbon atoms.

15. A tolan compound as claimed in claim 13, wherein $R^2$ is F, $OCF_3$, straight chain alkyl or alkoxy having 1 to 10 carbon atoms, or alkenyl or alkenyloxy having 2 to 10 carbon atoms.

16. A tolan compound as claimed in claim 13, wherein Z is —$CH_2CH_2$—, —COO—, or a single bond.

17. A tolan compound as claimed in claim 13, wherein m is 1 or 0.

18. A tolan compound as claimed in claim 13, wherein A is

19. A tolane compound of the following formula

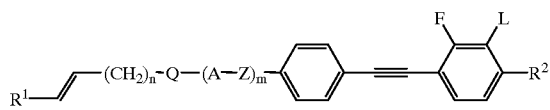

in which $R^1$ is H or an alkyl radical having 1–12 carbon atoms which is unsubstituted, monosubstituted by CN or CF, or monosubstituted to perhalosubstituted by halogen, where one or more non-adjacent $CH_2$ groups in these radicals are, independently of one another, each optionally replaced by —CH=CH—, —O—, —S—, —CO—,

—CO—O—, —O—CO—, or —O—CO—O—, $R^2$ is alkyl or alkoxy having 1 to 10 carbon atoms which is unsubstituted or monosubstituted to perhalosubstituted by halogen; alkenyl or alkenyloxy having 2 to 10 carbon atoms which is unsubstituted or at least monosubstituted by —CN, $CF_3$ or —F; or —F, —Cl, —$CF_3$, —$OCHF_2$, —$OCF_3$, —$OCHFCF_3$ or —$OCF_2CF_3$, L is either H or F, Q is —O— or a single bond A are independently a trans-1,4-cyclohexylene radical, in which one or more non-adjacent $CH_2$ groups are optionally replaced by —O— and/or —S—; or a 1,4-cyclohexenylene radical where the rings are optionally substituted by CN, Cl or F, Z are, independently of one another, —CO—O—, —O—CO—, —$CH_2O$—, —O—, —O—$CH_2$—, —$CH_2CH_2$—, —CH=CH—, —C≡C— or a single bond, n is 0, 1, 2, 3 or 4 and m is 0, 1 or 2, with the proviso that compounds in which m is 0 and simultaneously $R^2$ is alkyl or alkoxy are excluded.

20. A tolan compound as claimed in claim 19, wherein $R^1$ is H, straight chain alkyl having 1 to 10 carbon atoms, alkenyl having 2 to 10 carbon atoms, or alkoxy having from 1 to 10 carbon atoms.

21. A tolan compound as claimed in claim 19, wherein $R^2$ is F, $OCF_3$, straight chain alkyl or alkoxy having 1 to 10 carbon atoms, or alkenyl or alkenyloxy having 2 to 10 carbon atoms.

22. A tolan compound as claimed in claim 19, wherein Z is —$CH_2CH_2$—, —COO—, or a single bond.

23. A tolan compound as claimed in claim 19, wherein m is 1 or 0.

24. A tolan compound as claimed in claim 4, wherein A is

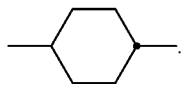

25. A tolan compound according to the following formula:

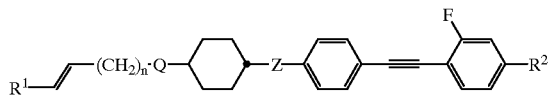

in which $R^1$ is H or an alkyl radical having 1–12 carbon atoms which is unsubstituted, monosubstituted by CN or CF, or monosubstituted to perhalosubstituted by halogen, where one or more non-adjacent CH, groups in these radicals are, independently of one another, each optionally replaced by —CH=CH—, —O—, —S—, —CO—,

—CO—O—, —O—CO—, or —O—COO—, $R^2$ is alkyl or alkoxy having 1 to 10 carbon atoms which is unsubstituted or monosubstituted to perhalosubstituted by halogen; alkenyl or alkenyloxy having 2 to 10 carbon atoms which is unsubstituted or at least monosubstituted by —CN, $CF_3$ or —F; or —F, —Cl, —$CF_3$, —$OCHF_2$, —$OCF_3$, —$OCHFCF_3$ or —$OCF_2CF_3$, Q is —O— or a single bond, z is —CO—O—, —O—CO—, —$CH_2O$—, —O—, —O—$CH_2$—, —$CH_2CH_2$—, —CH=CH—, —C≡C— or a single bond, and n is 0, 1, 2, 3 or 4.

26. A tolan compound according to the following formula:

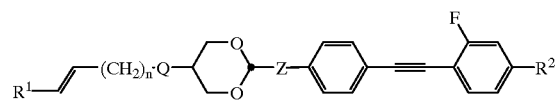

in which $R^1$ is H or an alkyl radical having 1–12 carbon atoms which is unsubstituted, monosubstituted by CN or CF, or monosubstituted to perhalosubstituted by halogen, where one or more non-adjacent CH, groups in these radicals are, independently of one another, each optionally replaced by —CH=CH—, —O—, —S—, —CO—,

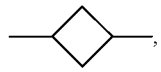

—CO—O—, —O—CO—, or —O—CO—O—, $R^2$ is alkyl or alkoxy having 1 to 10 carbon atoms which is unsubstituted or monosubstituted to perhalosubstituted by halogen; alkenyl or alkenyloxy having 2 to 10 carbon atoms which is unsubstituted or at least monosubstituted by —CN, $CF_3$ or —F; or —F, —Cl, —$CF_3$, —$OCHF_2$, —$OCF_3$, —$OCHFCF_3$ or —$OCF_2CF_3$, Q is —O— or a single bond, z is —CO—O—, —O—CO—, —$CH_2O$—, —O—, —O—$CH_2$—, —$CH_2CH_2$—, —CH=CH—, —C≡C— or a single bond, and n is 0, 1, 2, 3 or 4.

27. An electro-optical display, comprising a tolan compound as claimed in claim 1.

28. An electro-optical display, comprising a tolan compound as claimed in claim 7.

29. An electro-optical display, comprising a tolan compound as claimed in claim 13.

30. An electro-optical display, comprising a tolan compound as claimed in claim 19.

* * * * *